US012712077B2

(12) United States Patent
Lu et al.

(10) Patent No.: US 12,712,077 B2
(45) Date of Patent: Aug. 18, 2026

(54) INFORMATION PROCESSING METHOD, MEDICAL IMAGE DIAGNOSTIC APPARATUS, AND INFORMATION PROCESSING SYSTEM

(71) Applicant: CANON KABUSHIKI KAISHA, Tokyo (JP)

(72) Inventors: Yujie Lu, Vernon Hills, IL (US); Liang Cai, Vernon Hills, IL (US); Ting Xia, Vernon Hills, IL (US); Jian Zhou, Vernon Hills, IL (US); Zhou Yu, Vernon Hills, IL (US)

(73) Assignee: CANON KABUSHIKI KAISHA, Tokyo (JP)

( * ) Notice: Subject to any disclaimer, the term of this patent is extended or adjusted under 35 U.S.C. 154(b) by 652 days.

(21) Appl. No.: 17/718,898

(22) Filed: Apr. 12, 2022

(65) Prior Publication Data

US 2023/0326596 A1 Oct. 12, 2023

(51) Int. Cl.
*G16H 50/20* (2018.01)
*A61B 6/00* (2024.01)
(Continued)

(52) U.S. Cl.
CPC ............ *G16H 50/20* (2018.01); *A61B 6/032* (2013.01); *A61B 6/12* (2013.01); *A61B 6/5258* (2013.01);
(Continued)

(58) Field of Classification Search
CPC ........ G16H 50/20; G16H 30/40; G16H 30/20; A61B 6/032; A61B 6/12; A61B 6/5258;
(Continued)

(56) References Cited

U.S. PATENT DOCUMENTS

2018/0061058 A1* 3/2018 Xu ............................ G06T 7/11
2019/0130562 A1 5/2019 Liu et al.
(Continued)

FOREIGN PATENT DOCUMENTS

WO WO 2018/039368 A1 3/2018
WO WO-2021199960 A1 * 10/2021 ............... A61B 8/12

OTHER PUBLICATIONS

Ju Xu et al. "Automatic Data Augmentation for 3D Medical Image Segmentation"; Peking University; Dec. 27, 2020.

*Primary Examiner* — Chan S Park
*Assistant Examiner* — Daniel C Chang
(74) *Attorney, Agent, or Firm* — Oblon, McClelland, Maier & Neustadt, L.L.P.

(57) ABSTRACT

A method of processing information acquired by imaging performed by a medical image diagnostic apparatus, the method including but not limited to at least one of (A) acquiring a training image volume including at least one three-dimensional object having an embedded three-dimensional feature having a first cross-sectional area in a first three-dimensional plane; selecting a second cross-sectional area in a second three-dimensional plane containing the embedded three-dimensional feature, wherein the second cross-sectional area is larger than the first cross-sectional area; and training an untrained neural network with an image of the second cross-sectional area generated from the training image volume; and (B) acquiring a first set of training data; determining a first distribution of tissue density information from the first set of training data; generating from the first set of training data a second set of training data by performing at least one of a tissue-density shifting process and a tissue-density scaling process; and training an untrained neural network with the first and second sets of training data to obtain a trained neural network.

10 Claims, 23 Drawing Sheets

(51) Int. Cl.

| | |
|---|---|
| ***A61B 6/03*** | (2006.01) |
| ***A61B 6/12*** | (2006.01) |
| ***G06N 3/08*** | (2023.01) |
| ***G06T 7/00*** | (2017.01) |
| ***G06T 7/11*** | (2017.01) |
| ***G06T 7/62*** | (2017.01) |
| ***G06T 12/30*** | (2026.01) |
| ***G16H 30/40*** | (2018.01) |

(52) U.S. Cl.
CPC ............. *G06N 3/08* (2013.01); *G06T 7/0012* (2013.01); *G06T 7/11* (2017.01); *G06T 7/62* (2017.01); *G06T 12/30* (2026.01); *G16H 30/40* (2018.01); *G06T 2207/10081* (2013.01); *G06T 2207/20081* (2013.01); *G06T 2207/20084* (2013.01); *G06T 2207/30052* (2013.01)

(58) Field of Classification Search
CPC .......... G06N 3/08; G06N 3/0464; G06N 3/09; G06T 7/0012; G06T 7/11; G06T 7/62; G06T 11/008; G06T 2207/10081; G06T 2207/20081; G06T 2207/20084; G06T 2207/30052
See application file for complete search history.

(56) References Cited

U.S. PATENT DOCUMENTS

| | | | | |
|---|---|---|---|---|
| 2020/0074701 | A1* | 3/2020 | Liang .................... | A61B 6/5217 |
| 2020/0090326 | A1 | 3/2020 | Fahni et al. | |
| 2021/0282719 | A1 | 9/2021 | Buckler et al. | |
| 2022/0198669 | A1* | 6/2022 | Chen ..................... | G06T 7/0016 |
| 2022/0405990 | A1* | 12/2022 | Chen ....................... | G06T 12/10 |

* cited by examiner

FIG. 1A

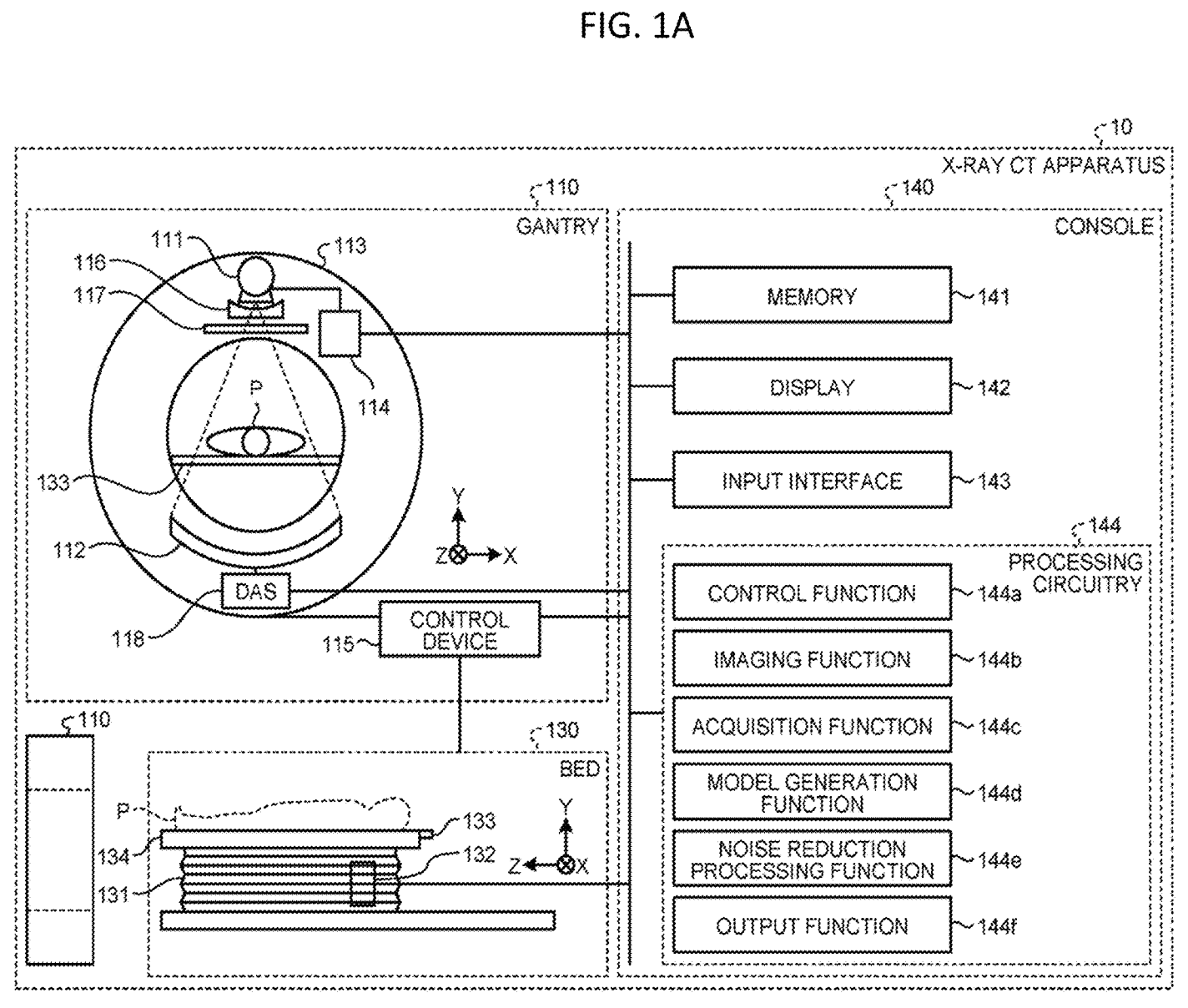

10 X-RAY CT APPARATUS
140 CONSOLE
141 MEMORY
142 DISPLAY
143 INPUT INTERFACE
144 PROCESSING CIRCUITRY
144a CONTROL FUNCTION
144b IMAGING FUNCTION
144c ACQUISITION FUNCTION
144d MODEL GENERATION FUNCTION
144e NOISE REDUCTION PROCESSING FUNCTION
144f OUTPUT FUNCTION
110 GANTRY
115 CONTROL DEVICE
118 DAS
130 BED

FIG. 1B

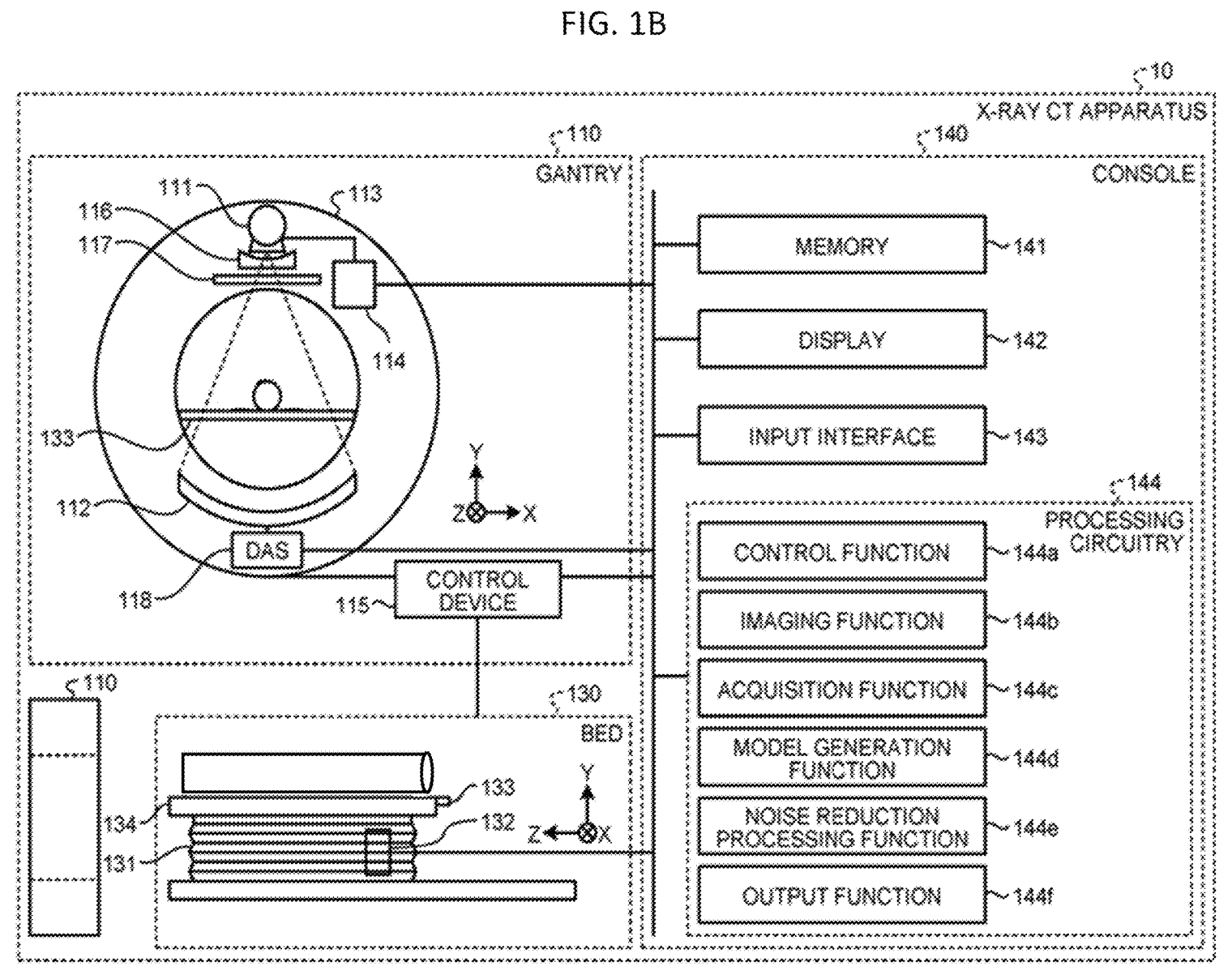

10 X-RAY CT APPARATUS

140 CONSOLE

141 MEMORY

142 DISPLAY

143 INPUT INTERFACE

144 PROCESSING CIRCUITRY

144a CONTROL FUNCTION

144b IMAGING FUNCTION

144c ACQUISITION FUNCTION

144d MODEL GENERATION FUNCTION

144e NOISE REDUCTION PROCESSING FUNCTION

144f OUTPUT FUNCTION

110 GANTRY 111, 112, 113, 114, 116, 117, 118, 133

115 CONTROL DEVICE

DAS

X, Y, Z

130 BED 131, 132, 133, 134

Split into noise image blocks

Perform random scaling

Converted into scaled noise image blocks

PROJECTION DATA $Y_{k-1}$
PROJECTION DATA $Y_k$
PROJECTION DATA $Y_{k+1}$
NOISE EXTRACTION PROCESSING
NOISE EXTRACTION PROCESSING
NOISE EXTRACTION PROCESSING
NOISE POOL 141a
Noise blocks (from Fig. 3B)
Noise blocks (from Fig. 3C)

PROJECTION DATA $Y_{t-1}$
PROJECTION DATA $Y_t$
PROJECTION DATA $Y_{t+1}$
RECONSTRUCTION PROCESSING R1
RECONSTRUCTION PROCESSING R2
RECONSTRUCTION PROCESSING R1
RECONSTRUCTION PROCESSING R2
RECONSTRUCTION PROCESSING R1
RECONSTRUCTION PROCESSING R2
IMAGE POOL 141b
IMAGE POOL 141c

FIG.5C
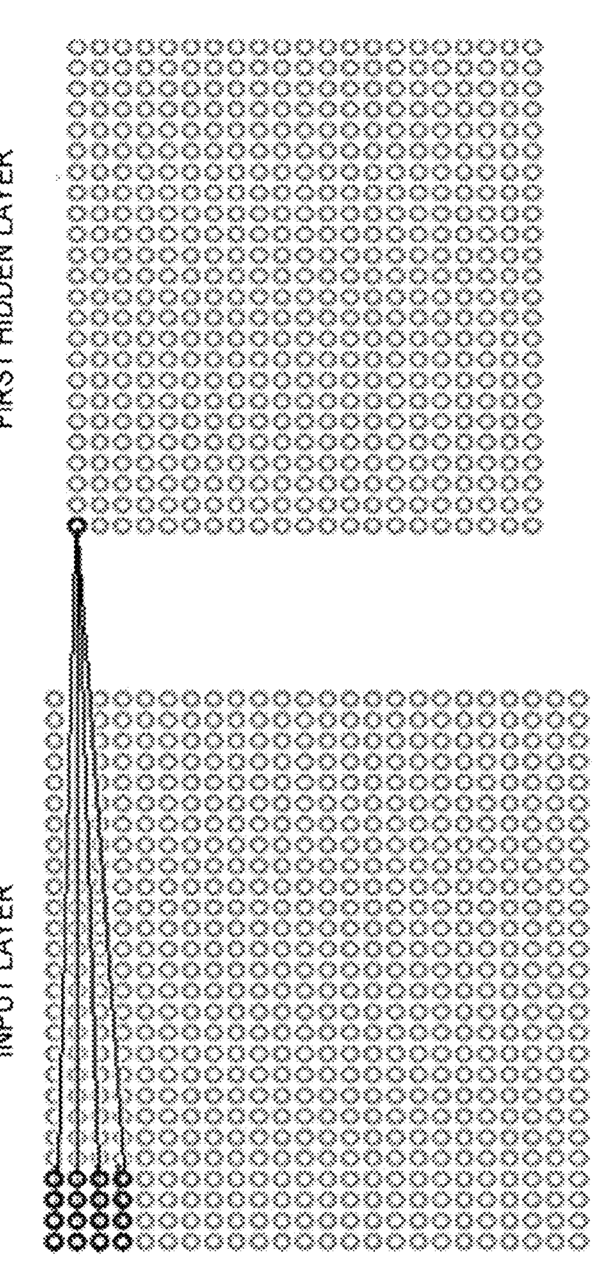
FIRST HIDDEN LAYER
INPUT LAYER

INFORMATION PROCESSING METHOD, MEDICAL IMAGE DIAGNOSTIC APPARATUS, AND INFORMATION PROCESSING SYSTEM

FIELD

Embodiments described herein relate generally to an information processing method, a medical image diagnostic apparatus, and an information processing system.

BACKGROUND

A medical image acquired from a subject by a medical image diagnostic apparatus may include noise due to various factors. In recent years, a noise reduction processing model based on machine learning has been proposed as one of noise reduction methods for reducing such noise. However, in order to obtain the noise reduction processing model, it is necessary to prepare training data used for the machine learning. Training data can be selected using at least one of region of interest-specific training data and scaled density-dependent training data.

BRIEF DESCRIPTION OF THE DRAWINGS

FIG. 1A is a block diagram of an exemplary configuration of an X-ray CT apparatus imaging a person as a subject according to an exemplary embodiment described below.

FIG. 1B is a block diagram of an exemplary configuration of an X-ray CT apparatus imaging a cylindrical phantom according to an exemplary embodiment described below.

FIG. 3C illustrates a third exemplary process of generating noise data according to an exemplary embodiment described below.

FIG. 5C illustrates a training process according to an exemplary embodiment described below.

DETAILED DESCRIPTION

Figure 2:
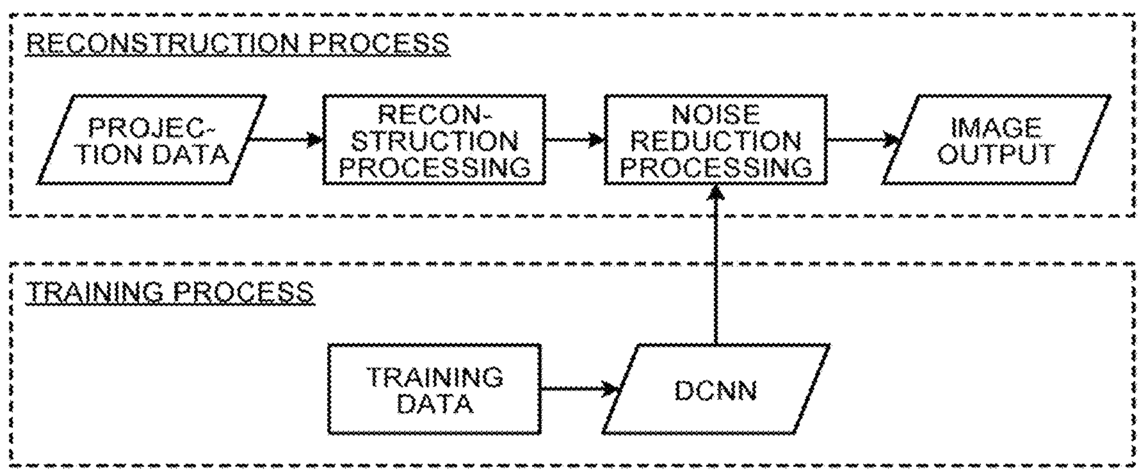
FIG. 2 illustrates an exemplary process performed by the X-ray CT apparatus.

An information processing method of an embodiment is a method of processing information acquired by imaging performed by a medical image diagnostic apparatus, the method including but not limited to: acquiring a training image volume including at least one three-dimensional object having an embedded three-dimensional feature having a first cross-sectional area in a first three-dimensional plane; selecting a second cross-sectional area in a second three-dimensional plane containing the embedded three-dimensional feature, wherein the second cross-sectional area is larger than the first cross-sectional area; and training an untrained neural network with an image of the second cross-sectional area generated from the training image volume.

An information processing method of another embodiment is method of processing information acquired by imaging performed by a medical image diagnostic apparatus, the information processing method including, but not limited to, the steps of: acquiring a first set of training data; determining a first distribution of tissue density information from the first set of training data; generating from the first set of training data a second set of training data by performing at least one of a tissue-density shifting process and a tissue-density scaling process; and training an untrained neural network with the first and second sets of training data to obtain a trained neural network.

The disclosure herein also describes an information processing apparatus including processing circuitry and/or computer instructions stored in a non-transitory computer readable storage medium for performing either or both of the above-noted methods.

Hereinafter, with reference to the accompanying drawings, an embodiment of an information processing method, a medical image diagnostic apparatus, and an information processing system will be described in detail.

In the present embodiment, X-ray CT will be described as an example of a medical image diagnostic modality. That is, in the present embodiment, an information processing method of information acquired by imaging performed by the X-ray CT will be described.

The X-ray CT is implemented, for example, in an X-ray CT apparatus 10 illustrated in FIG. 1A. FIG. 1A is a block diagram illustrating an example of a configuration of the X-ray CT apparatus 10 according to a first embodiment. For example, the X-ray CT apparatus 10 has a gantry 110, a bed 130, and a console 140.

In FIG. 1A, it is assumed that the longitudinal direction of a rotating shaft of a rotating frame 113 or a tabletop 133 of the bed 130 in a non-tilted state is a Z axis direction. Furthermore, it is assumed that an axial direction orthogonal to the Z axis direction and horizontal to a floor surface is an X axis direction. Furthermore, it is assumed that an axial direction orthogonal to the Z axis direction and perpendicular to the floor surface is a Y axis direction. Note that FIG. 1A illustrates the gantry 110 drawn from a plurality of directions for convenience of description and the X-ray CT apparatus 10 has one gantry 110.

The gantry 110 includes an X-ray tube 111, an X-ray detector 112, the rotating frame 113, an X-ray high voltage device 114, a control device 115, a wedge 116, a collimator 117, and a data acquisition system (DAS) 118.

The X-ray tube 111 is a vacuum tube having a cathode (filament) that generates thermoelectrons and an anode (target) that generates X-rays in response to a collision of thermoelectrons. The X-ray tube 111 emits the thermoelectrons toward the anode from the cathode by the application of a high voltage from the X-ray high voltage device 114, thereby generating the X-rays to be emitted to a subject P.

The X-ray detector 112 detects the X-rays emitted from the X-ray tube 111 and passed through the subject P, and outputs a signal corresponding to the dose of the detected X-rays to the DAS 118. The X-ray detector 112, for example, includes a plurality of detection element arrays in which a plurality of detection elements are arranged in a channel direction (channel direction) along one arc centered on a focal point of the X-ray tube 111. The X-ray detector 112, for example, has a structure in which the detection element arrays with the detection elements arranged in the channel direction are arranged in a row direction (slice direction and row direction).

For example, the X-ray detector 112 is an indirect conversion type detector having a grid, a scintillator array, and a photosensor array. The scintillator array has a plurality of scintillators. Each of the scintillators has a scintillator crystal that outputs light with a photon quantity corresponding to an incident X-ray dose. The grid has an X-ray shielding plate that is disposed on the surface of the scintillator array on an X-ray incident side and absorbs scatted X-rays. The grid may also be referred to as a collimator (a one-dimensional collimator or a two-dimensional collimator). The photosensor array has a function of converting light into an electrical signal corresponding to the amount of light from the scintillator, and has, for example, photosensors such as photodiodes. Note that the X-ray detector 112 may be a direct conversion type detector having a semiconductor element that converts the incident X-rays into electrical signals.

The rotating frame 113 is an annular frame that supports the X-ray tube 111 and the X-ray detector 112 so as to face each other and rotates the X-ray tube 111 and the X-ray detector 112 by the control device 115. For example, the rotating frame 113 is a casting made of aluminum. Note that the rotating frame 113 can further support the X-ray high voltage device 114, the wedge 116, the collimator 117, the DAS 118 and the like, in addition to the X-ray tube 111 and the X-ray detector 112. Moreover, the rotating frame 113 can further support various configurations not illustrated in FIG. 1*a*. Hereinafter, in the gantry 110, the rotating frame 113 and a part, which rotationally moves with the rotating frame 113, are also referred to as a rotating part.

The X-ray high voltage device 114 has electric circuitry such as a transformer and a rectifier, and has a high voltage generation device that generates a high voltage to be applied to the X-ray tube 111 and an X-ray control device that controls an output voltage corresponding to the X-rays generated by the X-ray tube 111. The high voltage generation device may be a transformer type device or an inverter type device. Note that the X-ray high voltage device 114 may be provided on the rotating frame 113, or may also be provided on a fixed frame (not illustrated).

The control device 115 has processing circuitry having a central processing unit (CPU) and the like, and a driving mechanism such as a motor and an actuator. The control device 115 receives input signals from an input interface 143 and controls the operations of the gantry 110 and the bed 130. For example, the control device 115 controls the rotation of the rotating frame 113, the tilt of the gantry 110, the operation of the bed 130, and the like. As an example, as control for tilting the gantry 110, the control device 115 rotates the rotating frame 113 around an axis parallel to the X axis direction based on information on an input inclination angle (tilt angle). Note that the control device 115 may be provided in the gantry 110 or may also be provided in the console 140.

The wedge 116 is an X-ray filter for adjusting the dose of the X-rays emitted from the X-ray tube 111. Specifically, the wedge 116 is an X-ray filter that attenuates the X-rays emitted from the X-ray tube 111 such that the X-rays emitted from the X-ray tube 111 to the subject P have a predetermined distribution. For example, the wedge 116 is a wedge filter or a bow-tie filter and is manufactured by processing aluminum and the like to have a predetermined target angle and a predetermined thickness.

The collimator 117 is a lead plate and the like for narrowing down the emission range of the X-rays having transmitted through the wedge 116 and forms a slit by a combination of a plurality of lead plates and the like. Note that the collimator 117 may also be referred to as an X-ray diaphragm. Furthermore, although FIG. 1A illustrates a case where the wedge 116 is disposed between the X-ray tube 111 and the collimator 117, the collimator 117 may be disposed between the X-ray tube 111 and the wedge 116. In such a case, the wedge 116 attenuates the X-rays, which are emitted from the X-ray tube 111 and whose emission range is limited by the collimator 117, by allowing the X-rays to pass therethrough.

The DAS 118 acquires X-ray signals detected by each detector element included in the X-ray detector 112. For example, the DAS 118 has an amplifier that performs an amplification process on electrical signals output from each detector element and an A/D converter that converts the electrical signals to digital signals, and generates detection data. The DAS 118 is implemented by, for example, a processor.

The data generated by the DAS 118 is transmitted from a transmitter having a light emitting diode (LED) provided on the rotating frame 113 to a receiver having a photodiode provided on a non-rotating part (for example, a fixed frame and the like and not illustrated in FIG. 1A) of the gantry 110 by optical communication, and is transmitted to the console 140. The non-rotating part is, for example, a fixed frame and the like that rotatably supports the rotating frame 113. Note that the data transmission method from the rotating frame 113 to the non-rotating part of the gantry 110 is not limited to the optical communication, and may adopt any non-contact type data transmission method or a contact type data transmission method.

The bed 130 is a device that places and moves the subject P to be scanned and includes a pedestal 131, a couch driving device 132, the tabletop 133, and a support frame 134. The pedestal 131 is a casing that supports the support frame 134 so as to be movable in a vertical direction. The couch driving device 132 is a driving mechanism that moves the tabletop 133, on which the subject P is placed, in a long axis direction of the tabletop 133 and includes a motor, an actuator and the like. The tabletop 133 provided on the upper surface of the support frame 134 is a plate on which the subject P is placed. Note that the couch driving device 132 may also move the support frame 134 in the long axis direction of the tabletop 133 in addition to the tabletop 133.

The console 140 has a memory 141, a display 142, the input interface 143, and processing circuitry 144. Although the console 140 is described as a separate body from the gantry 110, the gantry 110 may include the console 140 or a part of each component of the console 140.

The memory 141 is implemented by, for example, a semiconductor memory element such as a random access memory (RAM) and a flash memory, a hard disk, an optical disk, and the like. For example, the memory 141 stores a computer program for circuitry included in the X-ray CT apparatus 10 to perform its functions. Furthermore, the memory 141 stores various information obtained by imaging the subject P. Furthermore, the memory 141 stores a noise reduction processing model generated by the processing circuitry 144 to be described below. Note that the memory 141 may be implemented by a server group (cloud) connected to the X-ray CT apparatus 10 via a network.

The display 142 displays various information. For example, the display 142 displays an image based on denoised data to be described below. Furthermore, for example, the display 142 displays a graphical user interface (GUI) for receiving various instructions, settings, and the like from a user via the input interface 143. For example, the display 142 is a liquid crystal display or a cathode ray tube (CRT) display. The display 142 may be a desktop type display, or may be composed of a tablet terminal and the like capable of wirelessly communicating with the body of the X-ray CT apparatus 10.

Although the X-ray CT apparatus 10 is described as including the display 142 in FIG. 1A, the X-ray CT apparatus 10 may include a projector instead of or in addition to the display 142. Under the control of the processing circuitry 144, the projector can perform projection onto a screen, a wall, a floor, the body surface of the subject P, and the like. As an example, the projector can also perform projection onto any plane, object, space, and the like by projection mapping.

The input interface 143 receives various input operations from a user, converts the received input operations into electrical signals, and outputs the electrical signals to the processing circuitry 144. For example, the input interface 143 is implemented by a mouse, a keyboard, a trackball, a switch, a button, a joystick, a touch pad for performing an input operation by touching an operation surface, a touch screen in which a display screen and a touch pad are integrated, non-contact input circuitry using an optical sensor, voice input circuitry, and the like. Note that the input interface 143 may be composed of a tablet terminal and the like capable of wirelessly communicating with the body of the X-ray CT apparatus 10. Furthermore, the input interface 143 may be circuitry that receives an input operation from a user by motion capture. As an example, the input interface 143 can receive a user's body movement, line of sight, and the like as an input operation by processing a signal acquired via a tracker or an image collected for a user. Furthermore, the input interface 143 is not limited to one including physical operation parts such as a mouse and a keyboard. For example, an example of the input interface 143 includes electric signal processing circuitry which receives an electric signal corresponding to an input operation from an external input device separately provided from the X-ray CT apparatus 10 and outputs the electric signal to the processing circuitry 144.

The processing circuitry 144 controls the overall operation of the X-ray CT apparatus 10 by performing a control function 144*a*, an imaging function 144*b*, an acquisition function 144*c*, a model generation function 144*d*, a noise reduction processing function 144*e*, and an output function 144*f*.

For example, the processing circuitry 144 reads a computer program corresponding to the control function 144*a* from the memory 141 and executes the read computer program, thereby controlling various functions, such as the imaging function 144*b*, the acquisition function 144*c*, the model generation function 144*d*, the noise reduction processing function 144*e*, and the output function 144*f*, based on various input operations received from a user via the input interface 143.

Furthermore, for example, the processing circuitry 144 reads a computer program corresponding to the imaging function 144*b* from the memory 141 and executes the read computer program, thereby imaging the subject P. For example, the imaging function 144*b* controls the X-ray high voltage device 114 to supply the X-ray tube 111 with a high voltage. With this, the X-ray tube 111 generates X-rays to be emitted to the subject P. Furthermore, the imaging function 144*b* controls the couch driving device 132 to move the subject P into an imaging port of the gantry 110. Furthermore, the imaging function 144*b* adjusts the position of the wedge 116 and the opening degree and position of the collimator 117, thereby controlling the distribution of the X-rays emitted to the subject P. Furthermore, the imaging function 144*b* controls the control device 115 to rotate the rotating part. Furthermore, while the imaging is performed by the imaging function 144*b*, the DAS 118 acquires X-ray signals from the respective detection elements in the X-ray detector 112 and generates detection data.

Furthermore, the imaging function 144*b* performs pre-processing on the detection data output from the DAS 118. For example, the imaging function 144*b* performs pre-processing, such as logarithmic transformation processing, offset correction processing, inter-channel sensitivity correction processing, and beam hardening correction, on the detection data output from the DAS 118. Note that the data subjected to the pre-processing is also described as raw data. Furthermore, the detection data before the pre-processing and the raw data subjected to the pre-processing are also collectively described as projection data.

Furthermore, for example, the processing circuitry 144 reads a computer program corresponding to the acquisition function 144*c* from the memory 141 and executes the read computer program, thereby acquiring noise data based on imaging a subject P and acquiring synthesized subject data based on first subject projection data obtained by imaging the subject P and combining with the noise data. Furthermore, for example, the processing circuitry 144 reads a computer program corresponding to the model generation function 144*d* from the memory 141 and executes the read computer program, thereby obtaining the noise reduction processing model by machine learning using the synthesized subject data and subject projection data obtained by imaging the subject P. Furthermore, for example, the processing circuitry 144 reads a computer program corresponding to the noise reduction processing function 144*e* from the memory 141 and executes the read computer program, thereby reducing noise in input subject data by the noise reduction processing model and obtaining denoised data. Furthermore, for example, the processing circuitry 144 reads a computer program corresponding to the output function 144*f* from the memory 141 and executes the read computer program, thereby outputting an image based on the denoised data. Details of processing performed by the acquisition function 144*c*, the model generation function 144*d*, the noise reduction processing function 144*e*, and the output function 144*f* will be described below.

In the X-ray CT apparatus 10 illustrated in FIG. 1A, the respective processing functions are stored in the memory 141 in the form of the computer programs executable by a computer. The processing circuitry 144 is a processor that performs a function corresponding to each computer program by reading and executing the computer program from the memory 141. In other words, the processing circuitry 144 having read the computer program has a function corresponding to the read computer program.

Note that, in FIG. 1A, it has been described that the control function 144*a*, the imaging function 144*b*, the acquisition function 144*c*, the model generation function 144*d*, the noise reduction processing function 144*e*, and the output function 144*f* are implemented by the single processing circuitry 144, but the processing circuitry 144 may be configured by combining a plurality of independent processors, and each processor may be configured to perform each function by executing each computer program. Furthermore, each processing function of the processing circuitry 144 may be performed by being appropriately distributed or integrated into a single circuit or a plurality of processing circuits.

Furthermore, the processing circuitry 144 may also perform the functions by using a processor of an external device connected via the network. For example, the processing circuitry 144 reads and executes the computer program corresponding to each function from the memory 141 and uses, as computation resources, a server group (cloud) connected to the X-ray CT apparatus 10 via the network, thereby performing each function illustrated in FIG. 1A.

Furthermore, although FIG. 1A illustrates only the single memory 141, the X-ray CT apparatus 10 may include a plurality of physically separated memories. For example, the X-ray CT apparatus 10 may separately include, as the memory 141, a memory that stores a computer program required when circuitry included in the X-ray CT apparatus 10 performs its function, a memory that stores various information obtained by imaging the subject P, and a memory that stores the noise reduction processing model.

In addition, FIG. 1B illustrates the X-ray CT apparatus 10 of FIG. 1A but imaging a phantom (e.g., cylindrical phantom) rather than a person acting as a subject. Although illustrated as a cylinder, the phantom may instead be another solid structure such as a rectangle or a square. In one embodiment, the phantom is a water-based phantom, although other materials may be used in different imaging contexts. The material may be selected based on its transmissivity of low dose X-rays in a substantially uniform manner such that any variations are due to noise.

So far, the configuration example of the X-ray CT apparatus 10 has been described. Under such a configuration, it is assumed that the processing circuitry 144 in the X-ray CT apparatus 10 can easily acquire a high-quality noise reduction processing model by the following processes to be described below.

First, a series of processes from the imaging of the subject P to the output of an image will be described with reference to FIG. 2. FIG. 2 is a diagram illustrating an example of a process by the X-ray CT apparatus 10. As illustrated in FIG. 2, the process by the X-ray CT apparatus 10 is roughly divided into a reconstruction process and a training process.

For example, in the reconstruction process, the imaging function 144*b* obtains projection data by imaging the subject P. Next, the noise reduction processing function 144*e* generates a reconstructed image (CT image data) by performing the reconstruction processing on the projection data. For example, the noise reduction processing function 144*e* generates the reconfigured image by performing the reconstruction processing using a filtered back-projection (FBP) method, a successive approximation reconstruction method, a successive approximation applied reconstruction method, and the like on the projection data. Furthermore, the noise reduction processing function 144*e* can also generate the reconfigured image by performing the reconstruction processing by a machine learning method. For example, the noise reduction processing function 144*e* generates the reconstructed image by a deep learning reconstruction (DLR) method.

The reconstructed image may include noise due to various factors. For example, although the image quality of the reconstructed image is improved as the dose of X-rays used for acquiring the projection data increases, it is preferable to suppress the dose of the X-rays from the standpoint of reducing the exposure dose of the subject P. Then, when the projection data is acquired using a low dose of X-rays, the reconstructed image may include noise. Furthermore, a high-accuracy reconstruction method such as the successive approximation reconstruction method generally has a high computational load, and for example, when it is desired to quickly acquire the reconstructed image, another low-accuracy reconstruction method is selected. Then, when the low-accuracy reconstruction method is used, the reconstructed image may include noise.

In this regard, the noise reduction processing function 144*e* performs noise reduction processing on the reconstructed image as illustrated in FIG. 2. For example, the noise reduction processing function 144*e* performs the noise reduction processing on the reconstructed image by the noise reduction processing model trained using training data. With this, the output function 144*f* can output an image based on a reconstructed image with reduced noise. For example, the output function 144*f* generates a display image based on the reconstructed image with reduced noise and allows the display 142 to display the display image.

In the following description, as an example, the noise reduction processing model is configured by a deep convolution neural network (DCNN) illustrated in FIG. 2. For example, the model generation function 144*d* performs the training process prior to the reconstruction process, thereby generating a DCNN that is functionalized to reduce noise in input data. Furthermore, the generated DCNN is stored in the memory 141, for example, and the noise reduction processing function 144*e* can appropriately read and use the DCNN.

The training data of FIG. 2 is composed of, for example, a pair of (a) clean data not substantially including noise and (b) noisy data including noise. For example, the clean data is a reconstructed image acquired using a high dose of X-rays and the noisy data is a reconstructed image acquired using a low dose of X-rays. Alternatively, the noisy data may be a simulation image generated by a noise simulator. For example, the noise simulator receives the input of the clean data and simulates noise, thereby generating noise-added noisy data. In such a case, the noise reduction processing function 144*e* can train the DCNN by deep learning an input of which is the noisy data and a target of which is the clean data. Note that a training method targeting the clean data is also described as noise-to-clean (N2C).

As another example, the training data of FIG. 2 is composed of a pair of first noisy data including noise and second noisy data including other noise independent of the noise in the first noisy data. These two pieces of noisy data can be generated by the noise simulator, for example. In such a case, the noise reduction processing function 144*e* can train the DCNN by deep learning an input of which is one noisy data and a target of which is the other noisy data. Note that a training method targeting the noisy data is also described as noise-to-noise (N2N).

However, it is not easy to acquire a required number of clean data for training the DCNN. This is because there are not many opportunities to perform high-dose imaging in clinical sites. Furthermore, there are imaging conditions and imaging parts where there are particularly few opportunities to perform the high-dose imaging. For example, the high-dose imaging is rarely performed on a part easily affected by X-rays such as eyes and bone marrow. Furthermore, even when the high-dose imaging is performed, noise may occur.

Furthermore, it is not easy to prepare the noisy data by simulation. That is, unless a complicated model is used, it is not possible to perform appropriate noise simulation, and there are imaging conditions, imaging parts and the like that are difficult to be accurately modeled. Unless the noise simulation is appropriately performed, the accuracy of the DCNN may also be reduced.

Particularly, it is difficult to simulate a plurality of independent sets of noise data. For example, when simulating the noises based on the clean data, the clean data may include noise. The noise included in the clean data serve as an obstacle in simulating the independent sets of noise data. Furthermore, in recent years, there are cases where very low-dose imaging is performed, whereas it is particularly difficult to simulate noise that occur in the very low-dose imaging.

That is, even when either the noise-to-clean training method and the noise-to-noise training method is adopted, difficulties arise in preparing training data and training the DCNN appropriately. In this regard, the processing circuitry 144 makes it possible to acquire training data by processes to be described below and to aid in acquiring a high quality DCNN. Specifically, in a first embodiment the processing circuitry 144 acquires noise data based on the data from a subject acquired for noise generation (where the subject is a person), acquires synthesized subject data based on the first subject projection data and the noise data, and acquires a DCNN by performing deep learning using the synthesized subject data and the second subject projection data. In the second embodiment, noise data is obtained by imaging a uniform phantom acting as a subject such that variations in a reconstructed image of the phantom corresponds to noise.

Figure 3A:
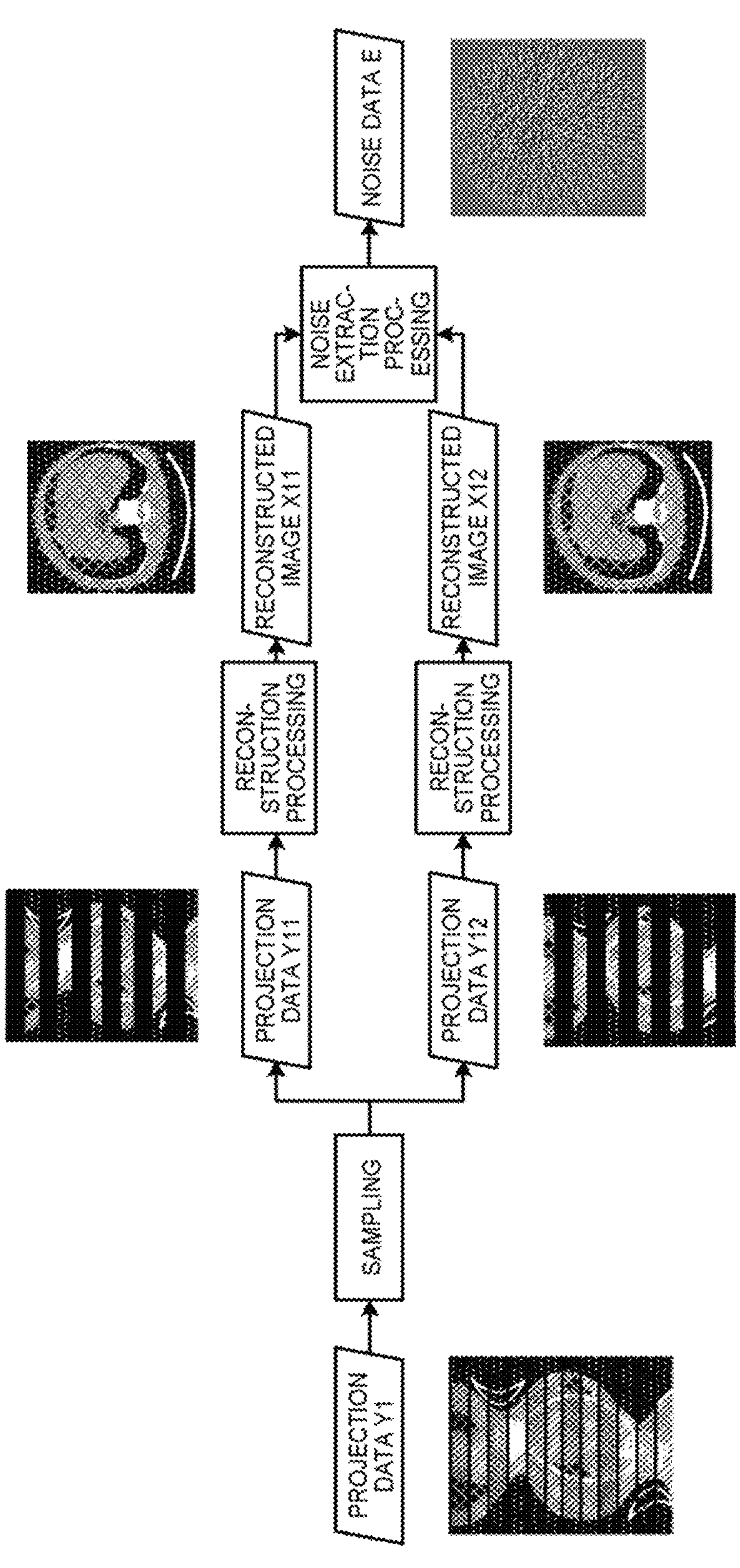
FIG. 3A illustrates a first exemplary process of generating noise data according to an exemplary embodiment described below.

First, a noise data acquisition process based on the data acquired for noise generation will be described with reference to FIG. 3A. FIG. 3A is a diagram for explaining noise data according to the first embodiment. In FIG. 3A, projection data Y1 will be described as an example of the data acquired from a subject for noise generation. The projection data Y1 is obtained by imaging that is performed by the X-ray CT apparatus 10, for example.

Here, the dose of X-rays used for acquiring the projection data Y1, a noise level of the projection data Y1, and the like are not particularly limited. For example, the imaging function 144*b* acquires the projection data Y1 by imaging a subject P11 by using a low dose of X-rays. Note that the subject P11 is an example of a subject P1. For example, as illustrated in FIG. 3, the projection data Y1 can be illustrated as a sinogram in which the channel direction of the X-ray detector 112 is set as a horizontal axis and the view (X-ray irradiation angle) is set as a vertical axis.

For example, the acquisition function 144*c* acquires projection data Y11 and projection data Y12 by sampling the projection data Y1. As an example, the acquisition function 144*c* acquires the projection data Y11 by sampling odd view data in the projection data Y1 and acquires the projection data Y12 by sampling even view data in the projection data Y1. That is, the acquisition function 144*c* alternately samples the projection data Y11 and the projection data Y12 for each view in the projection data Y1. Note that the projection data Y11 and the projection data Y12 are examples of a first subset and a second subset. The projection data Y11 and the projection data Y12 are data having a view number corresponding to a half of the projection data Y1.

Note that the sampling of the projection data Y1 can be variously modified. For example, the acquisition function 144*c* may alternately sample the projection data Y11 and the projection data Y12 for each of a plurality of views in the projection data Y1. Furthermore, for example, the acquisition function 144*c* may alternately sample the projection data Y11 and the projection data Y12 for each random number of views in the projection data Y1.

Furthermore, the acquisition function 144*c* may sample all the views of the projection data Y1, or sample some of the views of the projection data Y1. For example, when the projection data Y1 is full data of "360°", the acquisition function 144*c* may perform sampling within a range in which half reconstruction can be performed. As an example, when a fan angle is "30°", the acquisition function 144*c* can extract a "210°" view starting from an arbitrary view in the projection data Y1 of "360°", and sample the projection data Y11 and the projection data Y12 from the "210°" view. Here, the acquisition function 144*c* can shift the starting point for extracting the "210°" view, thereby extracting a plurality of "210°" views. That is, the acquisition function 144*c* can acquire a plurality of pairs of the projection data 11 and the projection data Y12 from the projection data Y1.

Next, the acquisition function 144*c* performs reconstruction processing on each of the projection data Y11 and the projection data Y12, thereby acquiring a reconstructed image X11 and a reconstructed image X12. For example, the acquisition function 144*c* performs the reconstruction processing by the FBP method, thereby acquiring the reconstructed image X11 and the reconstructed image X12. Note that the reconstructed image X11 and the reconstructed image X12 are examples of a first reconstructed image and a second reconstructed image.

Next, the acquisition function 144*c* acquires noise data ε based on the reconstructed image X11 and the reconstructed image X12. The noise data ε is, for example, data indicating noise intensity at each position in an image space. That is, the noise data ε is not a simple numerical value, such as an SD value, and is data indicating a spatial distribution of noise.

For example, the acquisition function 144_c_ acquires the noise data ε by performing difference processing between the reconstructed image X11 and the reconstructed image X12. For example, the acquisition function 144_c_ acquires the noise data ε by calculating, for each pixel, a difference in pixel values between corresponding pixels between the reconstructed image X11 and the reconstructed image X12.

Here, the projection data Y11 and the projection data Y12 are data obtained from the same object, and are data sampled such that overlap does not occur. Accordingly, the reconstructed image X11 and the reconstructed image X12 based on the projection data Y11 and the projection data Y12 have noise independent of each other. For example, the reconstructed image X11 and the reconstructed image X12 have the same noise level as when imaging is performed with a dose corresponding to a half of the dose used for acquiring the projection data Y1. Note that there is no need to strictly control the sampling so as not to cause overlap, and small amount of overlap, such as overlap of only one view, may be allowed.

Note that the noise data ε can also include various image artifacts as noise. That is, when the image artifacts are included in the reconstructed image X11 and the reconstructed image X12, the noise data ε includes the image artifacts as noise. When such noise data ε is used for training, DCNN to be described below is functionalized to reduce various noise including the image artifacts.

As an example, the acquisition function 144_c_ can acquire the noise data ε by a computation formula of $\varepsilon i=\alpha\ (x1-x2)$. εi denotes a pixel value of the noise data ε at a position i. Furthermore, x1 denotes a pixel value of the reconstructed image X11 at the position i. Furthermore, x2 denotes a pixel value of the reconstructed image X12 at the position i.

Furthermore, α denotes a parameter for adjusting a noise level. That is, the acquisition function 144_c_ can generate various noise data ε with adjusted noise levels by adjusting the value of α. For example, when α is set to a value larger than "0.5", the noise data ε indicates noise generated when imaging is performed with a dose smaller than the dose used for acquiring the projection data Y1. The acquisition function 144_c_ may set α to a fixed value or change the value of α. When changing the value of α, the acquisition function 144_c_ can acquire the noise data ε for each value of α.

Figure 4A:
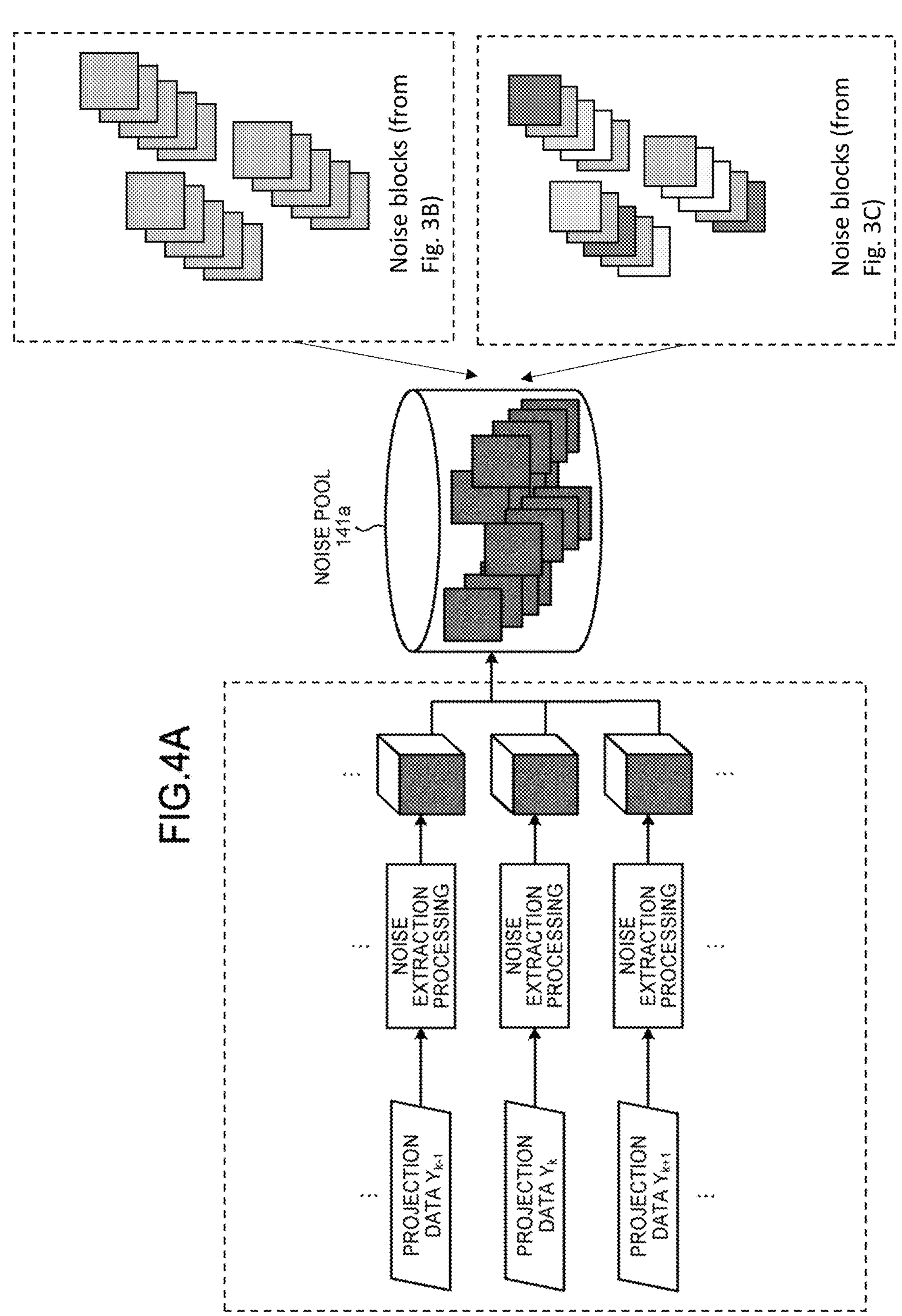
FIG. 4A illustrates a training process according to an exemplary embodiment described below.

As described above, the acquisition function 144_c_ acquires the noise data ε based on the projection data Y1 obtained from the subject P11 by the imaging performed by the X-ray CT apparatus 10. Similarly, the acquisition function 144_c_ acquires a plurality of noise data based on a plurality of projection data. For example, as illustrated in FIG. 4A, the acquisition function 144_c_ performs noise extraction processing on each of a plurality of projection data such as projection data Yk−1, projection data Yk, and projection data Yk+1, and allows the extracted noise data to be stored in a noise pool 141_a_. Note that the noise pool 141_a_ is an example of the memory 141. Furthermore, FIG. 4A is a diagram for explaining a training process according to the first embodiment.

As an example of a training process for using noise data from the noise pool 141_a_, the acquisition function 144_c_ generates volume data indicating a noise distribution for each of the projection data such as the projection data Yk−1, the projection data Yk, and the projection data Yk+1, and allows a plurality of two-dimensional data obtained by dividing the volume data to be stored in an image pool 141_b_ as noise data. Alternatively, the acquisition function 144_c_ generates volume data indicating a noise distribution for each of the projection data such as the projection data Yk−1, the projection data Yk, and the projection data Yk+1, and allows the volume data to be stored in the image pool 141_b_ as noise data. That is, the noise data may be managed as three-dimensional data or two-dimensional data.

Here, the projection data Yk−1, the projection data Yk, and the projection data Yk+1 illustrated in FIG. 4A are examples of the data acquired from a subject for noise generation. The projection data Yk−1, the projection data Yk, and the projection data Yk+1 may be data acquired from the subject P11, or may be data acquired from a subject other than the subject P11. Furthermore, the projection data Yk−1, the projection data Yk, and the projection data Yk+1 may be data obtained by the imaging performed by the X-ray CT apparatus 10, or may be data obtained by imaging performed by an X-ray CT apparatus different from the X-ray CT apparatus 10. The data acquired from a subject for noise generation may be data obtained by low-dose imaging, and thus can be acquired relatively easily.

Here, the acquisition function 144_c_ can also increase the number of the noise data stored in the noise pool 141_a_, by various methods. For example, the acquisition function 144_c_ can change the reconstruction method performed when generating the noise data, thereby generating a plurality of noise data. Furthermore, for example, the acquisition function 144_c_ can rotate the noise data by "90°", thereby obtaining four pieces of noise data. With this, the acquisition function 144_c_ can acquire more various noise data. The acquisition function 144_c_ may adjust the number of the noise data stored in the noise pool 141_a_ to be the same as the number of the first subject projection data stored in the image pool 141_b_ to be described below.

Figure 3B:
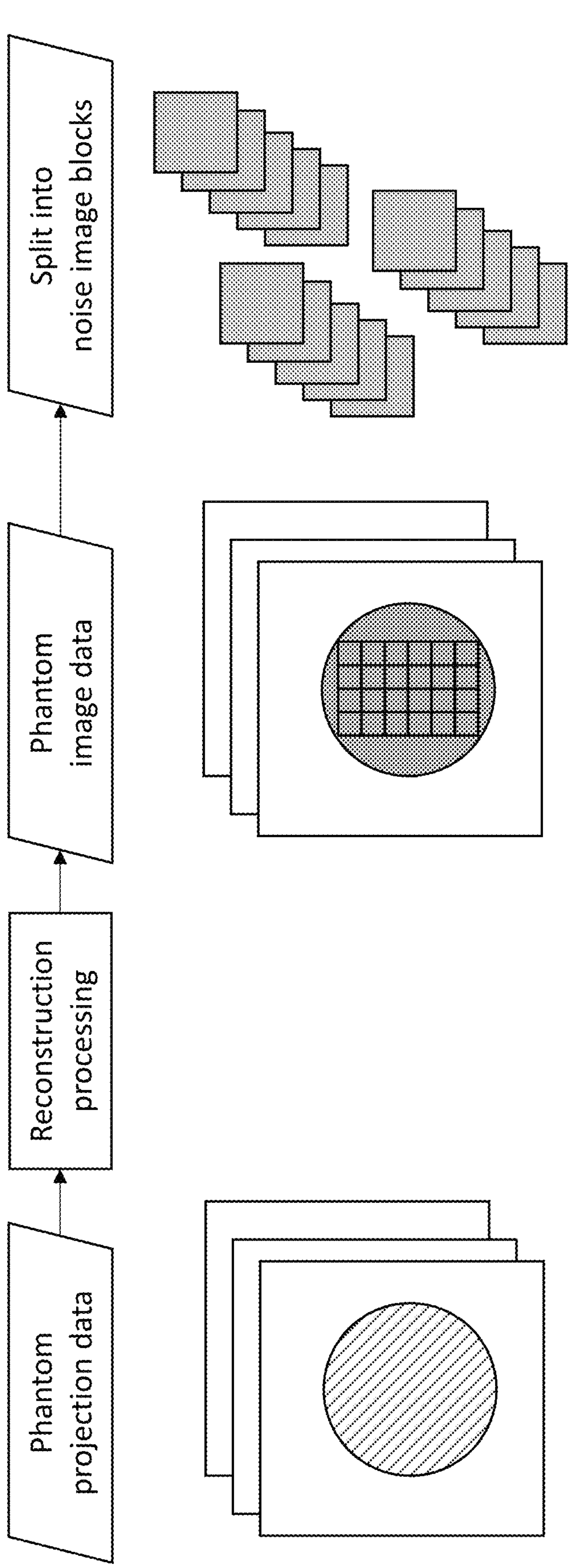
FIG. 3B illustrates a second exemplary process of generating noise data according to an exemplary embodiment described below.

As shown in FIG. 3B, noise data may instead (or in addition) be generated by acquiring imaging data obtained by imaging a phantom (e.g., using the configuration of FIG. 1B). As shown in FIG. 3B, a process partially paralleling FIG. 3A generates images from projection data. Although FIG. 3B illustrates imaging a cylindrical phantom rather than a person acting as a subject, the phantom may instead be another solid structure such as a rectangle or a square. In one embodiment, the phantom is a water-based phantom, although other materials may be used in different imaging contexts. The material may be selected based on its transmissivity of low dose X-rays in a substantially uniform manner such that any variations are due to noise. As illustrated in FIG. 3B, a first set of projection data (illustrated as having a circle in a square block of imaging data) can be used to generate a first reconstructed image that is then split into smaller reconstructed images or patches that are independent of each other and that therefore can be used as noise images to be added to the noise pool 141_a_. FIG. 3B also shows second and third sets of projection data that can be used to generate second and third reconstructed images that are then split into smaller reconstructed images or patches that are independent of each other and that therefore can be used as noise images. Although illustrated as using three sets of projection data, any number of sets can be generated, and the conditions under which the projection data is obtained can be varied to more closely match the data to which the resulting noise images are going to be added.

Figure 3C:
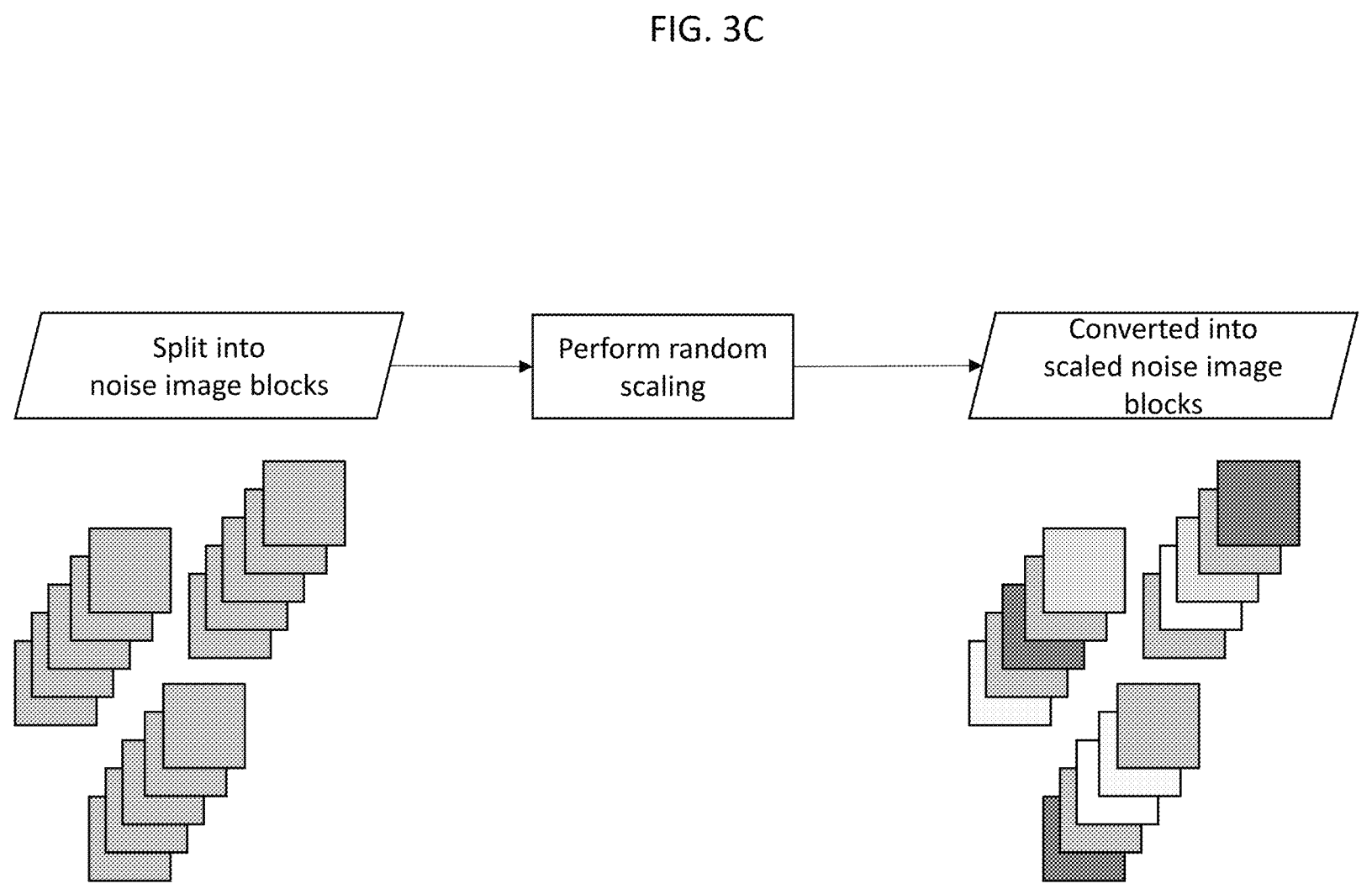

In one embodiment shown in FIG. 3C, the patches of reconstructed noise images can additionally be subjected to additional random scaling (e.g., between 0.1 and 1) on a patch-by-patch basis to make the resulting noise more diverse. As shown in FIG. 3C, the reconstructed image patches are illustrated as being various shades of grey which represent a specific random value having been applied to the patch. For example, in a very light patch, the scaling factor of 0.1 could have been applied to a first noise patch such that each pixel therein is 0.1 times its original value. Similarly, dark grey patches can symbolize a scaling factor of 0.7 having been applied to all of the pixels of its corresponding original patch.

In a first sub-embodiment, only original patches without scaling factors are used as noise data and added to the noise pool 141*a*. In a second sub-embodiment, patches with scaling factors having been applied are used as noise data but not the original patches. In a third sub-embodiment, both original patches and patches with scaling factors having been applied are used as noise data.

As shown in FIG. 4A, the noise pool 141*a* includes at least one of the types of noise data described herein, and the noise pool can be configured to include any combination of types of noise data including all of the types of noise data described herein.

Figure 4B:
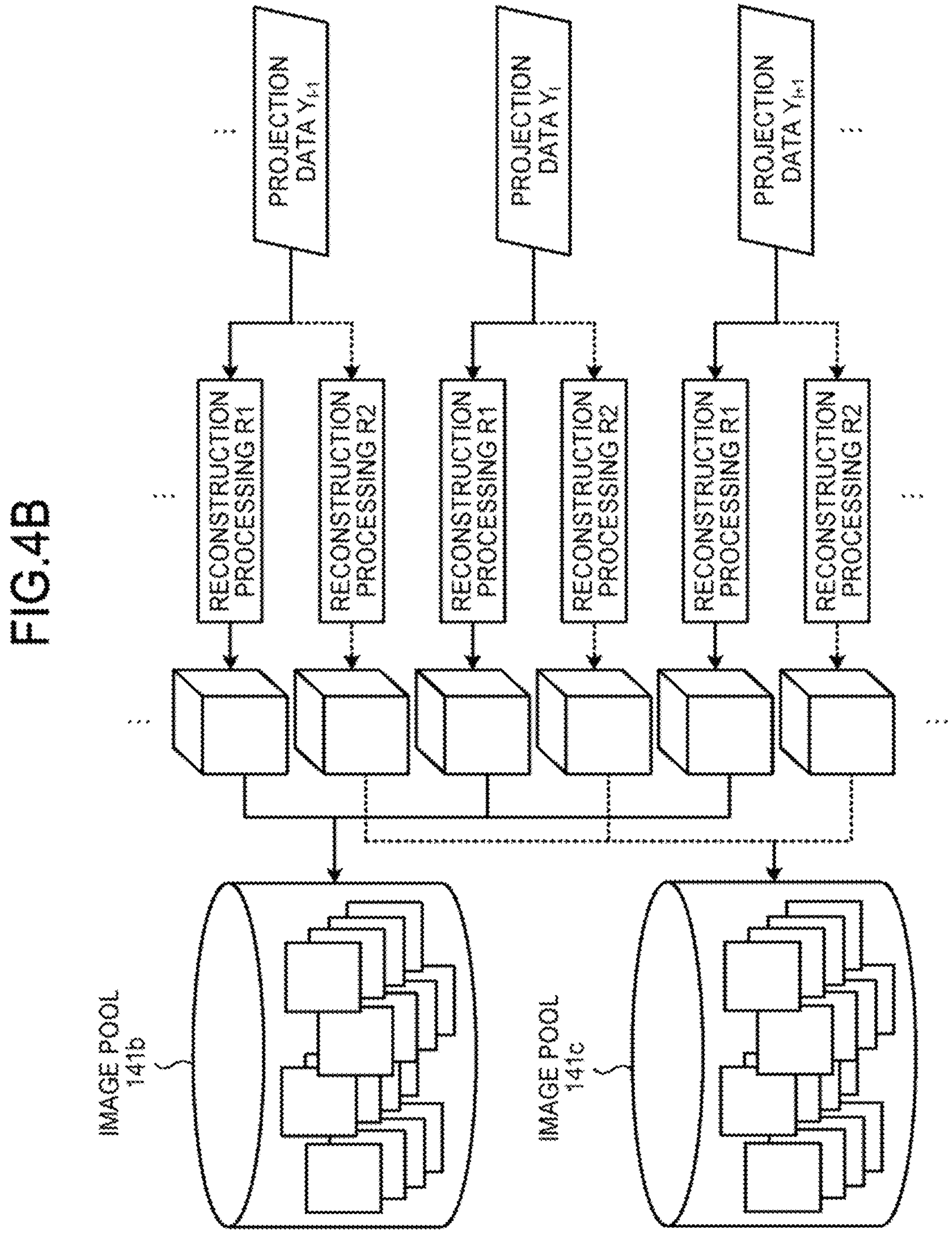
FIG. 4B illustrates a training process according to an exemplary embodiment described below.

Next, two additional sets of projection subject data will be described with reference to FIG. 4B. Those sets of subject data are generally referred to herein as second subject projection data and third subject projection data. FIG. 4B is a diagram for explaining a training process according to the first embodiment. For example, the acquisition function 144*c* first acquires a plurality of projection data such as projection data Yl−1, projection data Yl, and projection data Yl+1 illustrated in FIG. 4B. Note that the projection data Yl−1, the projection data Yl and the projection data Y1+1 are examples of third subject projection data.

For example, the projection data Yl−1, the projection data Yl, and the projection data Yl+1 are data different from the data acquired from a subject for noise generation (for example, the projection data Yk−1, the projection data Yk, the projection data Yk+1, and the like). For example, the projection data Yl−1, the projection data Yl, and the projection data Yl+1 are data acquired from a subject different from the subject of the data acquired from a subject for noise generation, or data acquired from the same subject at different dates and times. In other words, the first subject projection data is data acquired from a subject different from the data acquired from a subject for noise generation, or data acquired at a date and time different from the data acquired from a subject for noise generation. Note that the projection data Yl−1, the projection data Yl, and the projection data Yl+1 may be data that partially or entirely overlap the data acquired from a subject for noise generation.

Furthermore, the projection data Yl−1, the projection data Yl, and the projection data Yl+1 may be data obtained by the imaging performed by the X-ray CT apparatus 10, or may be data obtained by imaging performed by an X-ray CT apparatus different from the X-ray CT apparatus 10. That is, the first subject projection data may be acquired by imaging performed by the same medical image diagnostic apparatus as the medical image diagnostic apparatus that has imaged the data acquired from a subject for noise generation (or that imaged the phantom), or the first subject projection data may be acquired by imaging performed by a same kind of but different medical image diagnostic apparatus as the medical image diagnostic apparatus that has imaged the data acquired from a subject for noise generation (or that imaged the phantom). The first subject projection data may be acquired by the same imaging system as that of the data acquired from a subject for noise generation (or that imaged the phantom), or may be acquired by a different imaging system. For example, when the data acquired from a subject for noise generation (or the phantom) is acquired by helical scan, the first subject projection data may be collected by non-helical scan.

Next, the acquisition function 144*c* performs reconstruction processing R1 and reconstruction processing R2 on each of the projection data. The reconstruction processing R1 and the reconstruction processing R2 may be different reconstruction methods or the same reconstruction method. For example, the acquisition function 144*c* performs the FBP as the reconstruction processing R1 and performs the successive approximation reconstruction method as the reconstruction processing R2.

For example, the acquisition function 144*c* performs the reconstruction processing R1 on the projection data Yl−1, and allows a generated reconstructed image to be stored in the image pool 141*b*. As an example, the acquisition function 144*c* divides the reconstructed image generated as volume data into a plurality of two-dimensional reconstructed images and allows the two-dimensional reconstructed images to be stored in the image pool 141*b*. Similarly, the acquisition function 144*c* performs the reconstruction processing R1 on the projection data Yl, and allows a generated reconstructed image to be stored in the image pool 141*b*. Similarly, the acquisition function 144*c* performs the reconstruction processing R1 on the projection data Yl+1, and allows a generated reconstructed image to be stored in the image pool 141*b*. The reconstructed images generated by the reconstruction processing R1 are examples of the first subject projection data. Furthermore, the image pool 141*b* is an example of the memory 141.

Furthermore, the acquisition function 144*c* performs the reconstruction processing R2 on the projection data Yl−1, and allows a generated reconstructed image to be stored in an image pool 141*c*. As an example, the acquisition function 144*c* divides the reconstructed image (volume data) into a plurality of two-dimensional reconstructed images and allows the two-dimensional reconstructed images to be stored in the image pool 141*c*. Similarly, the acquisition function 144*c* performs the reconstruction processing R2 on the projection data Yl, and allows a generated reconstructed image to be stored in the image pool 141*c*. Similarly, the acquisition function 144*c* performs the reconstruction processing R2 on the projection data Yl+1, and allows a generated reconstructed image to be stored in the image pool 141*c*. The reconstructed images generated by the reconstruction processing R2 are examples of the second subject projection data. That is, the second subject projection data is data acquired by imaging a same subject as that of the first subject projection data. Furthermore, the image pool 141*c* is an example of the memory 141.

Note that the reconstruction field of views (rFOVs) of the first subject projection data and the second subject projection data may be a fixed size or may be changed in size. For example, the acquisition function 144*c* can also generate a plurality of first subject projection data, whose rFOVs have been changed, from one projection data. With this, the acquisition function 144*c* can acquire more various data as the first subject projection data and the second subject projection data.

Figure 4C:
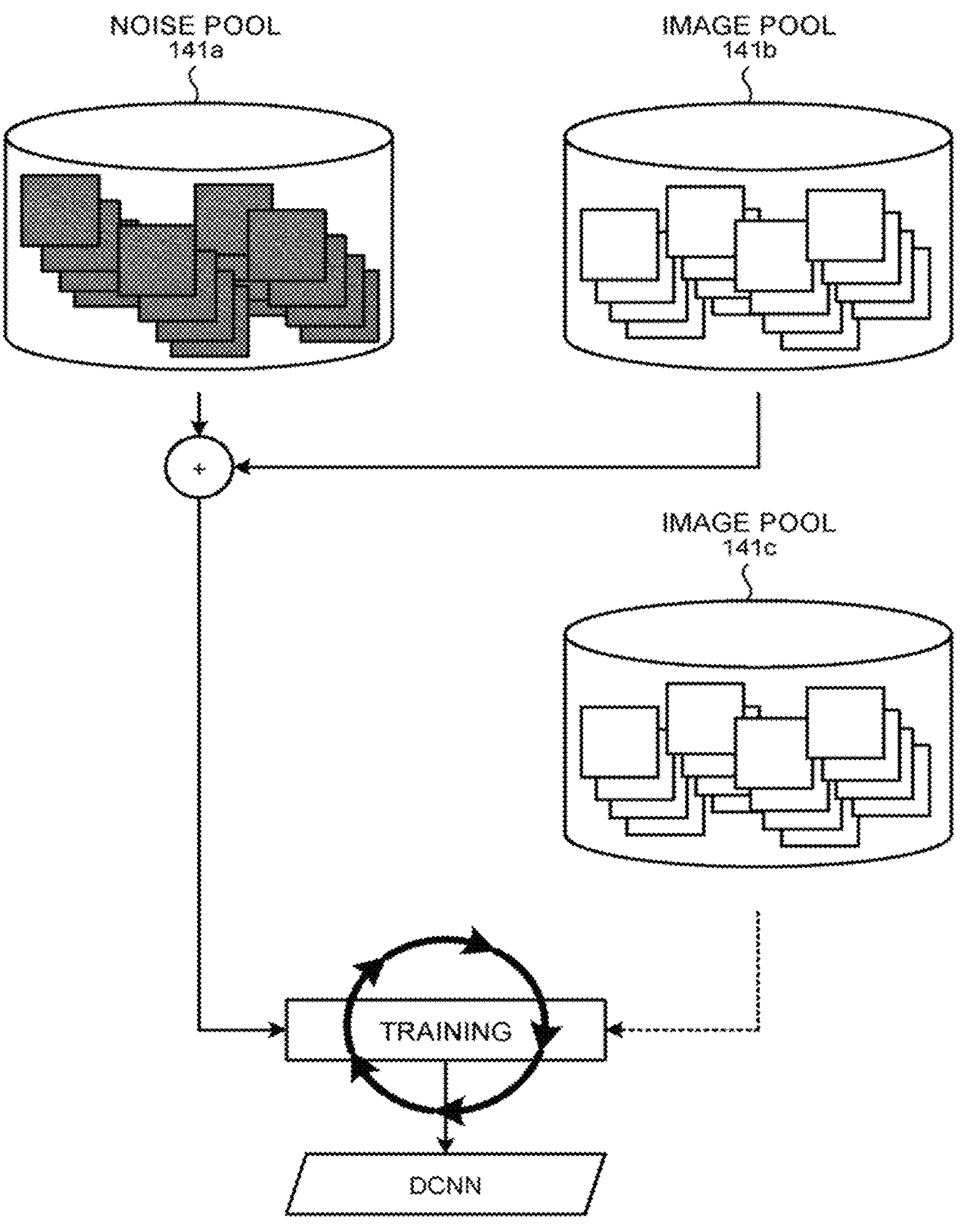
FIG. 4C illustrates a training process according to an exemplary embodiment described below.

As described above, the acquisition function 144*c* allows the noise data (e.g., based on at least one of the data acquired from a subject for noise generation and the imaging of a phantom) to be stored in the noise pool 141*a*, allows the first subject projection data to be stored in the image pool 141*b*, and allows the second subject projection data to be stored in the image pool 141*c*. Next, as illustrated in FIG. 4C, the acquisition function 144*c* reads the noise data and the first subject projection data from the noise pool 141*a* and the image pool 141*b*, and acquires synthesized subject data, in which noise based on the noise data are added to the first subject projection data, based on the first subject projection data and the noise data. FIG. 4C is a diagram for explaining a training process according to the first embodiment.

For example, the acquisition function 144*c* acquires the synthesized subject data by summing pixel values for each pixel in the noise data and the first subject projection data. In other words, the acquisition function 144*c* acquires the synthesized subject data by synthesizing the noise data and the first subject projection data. Here, the acquisition function 144*c* can acquire the synthesized subject data for each combination of the noise data stored in the noise pool 141*a* and the first subject projection data stored in the image pool 141*b*. Furthermore, the acquisition function 144*c* can also acquire a plurality of synthesized subject data by shifting the position of the noise data with respect to the first subject projection data.

Note that the acquisition function 144*c* may adjust a weight when synthesizing the noise data and the first subject projection data. For example, the acquisition function 144*c* adjusts the noise level of the noise data by the aforementioned parameter $\alpha$ and then adds the noise level to the first subject projection data. As an example, the aforementioned noise data corresponds to a difference between the reconstructed image X11 and the reconstructed image X12 in FIG. 3A, and has undergone normalization (averaging effect). Note that the addition and the subtraction produce similar averaging effects. The acquisition function 144*c* can correct the influence of the averaging effect by performing weighting in the synthesizing process. As another example, the acquisition function 144*c* can generate various synthesized subject data with varying doses by performing various types of weighting.

Then, as illustrated in FIG. 4C, the model generation function 144*d* performs training using the synthesized subject data and the second subject projection data read from the image pool 141*c*, thereby obtaining a DCNN functionalized to perform noise reduction processing. Specifically, the model generation function 144*d* obtains the DCNN by performing deep learning an input of which is the synthesized subject data and a target of which is the second subject projection data. Note that the DCNN illustrated in FIG. 4C is an example of the noise reduction processing model.

Figure 4D:
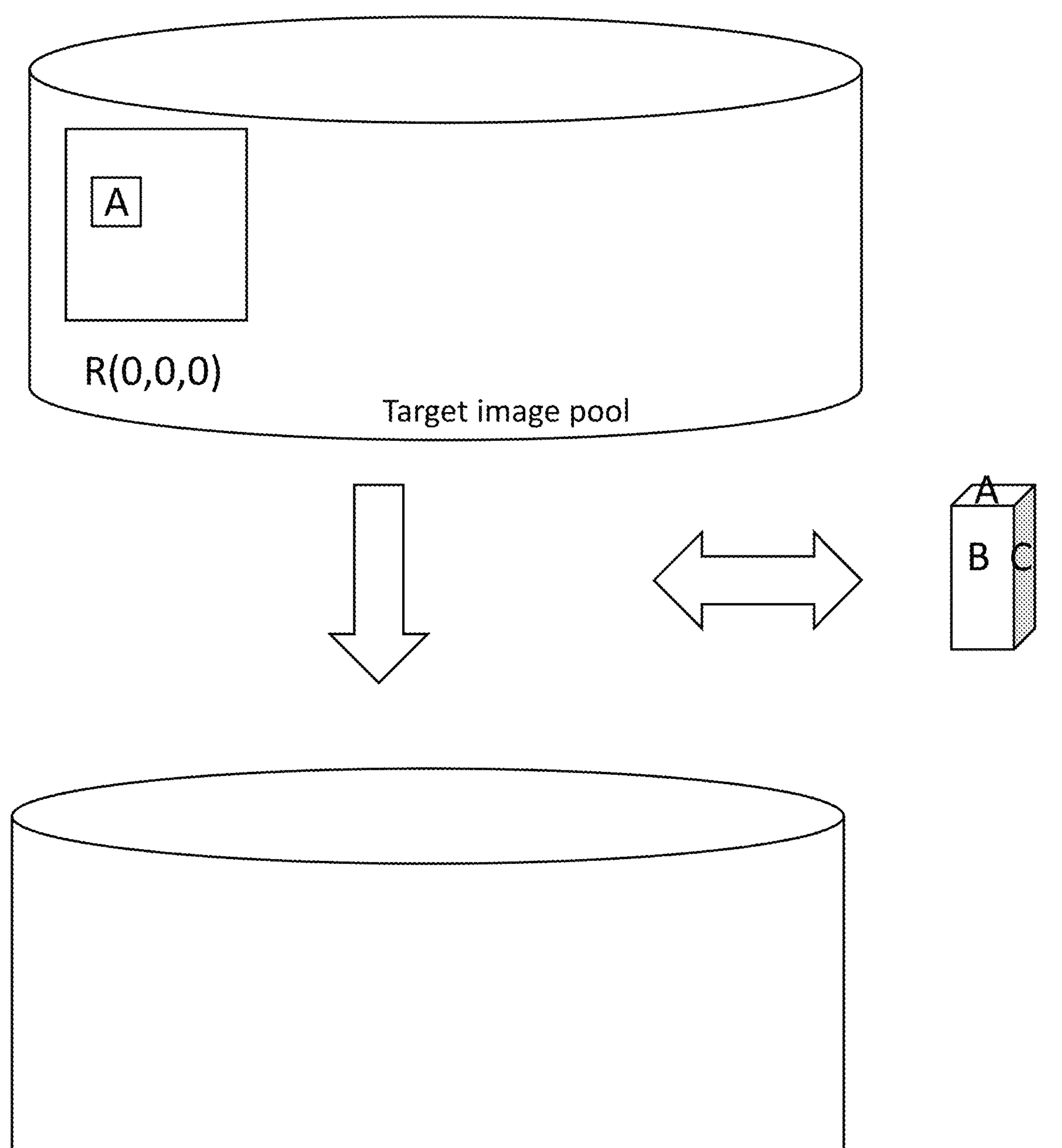
FIG. 4D illustrates a process of replacing target training data for use in a medical image training process.
Figure 4E:
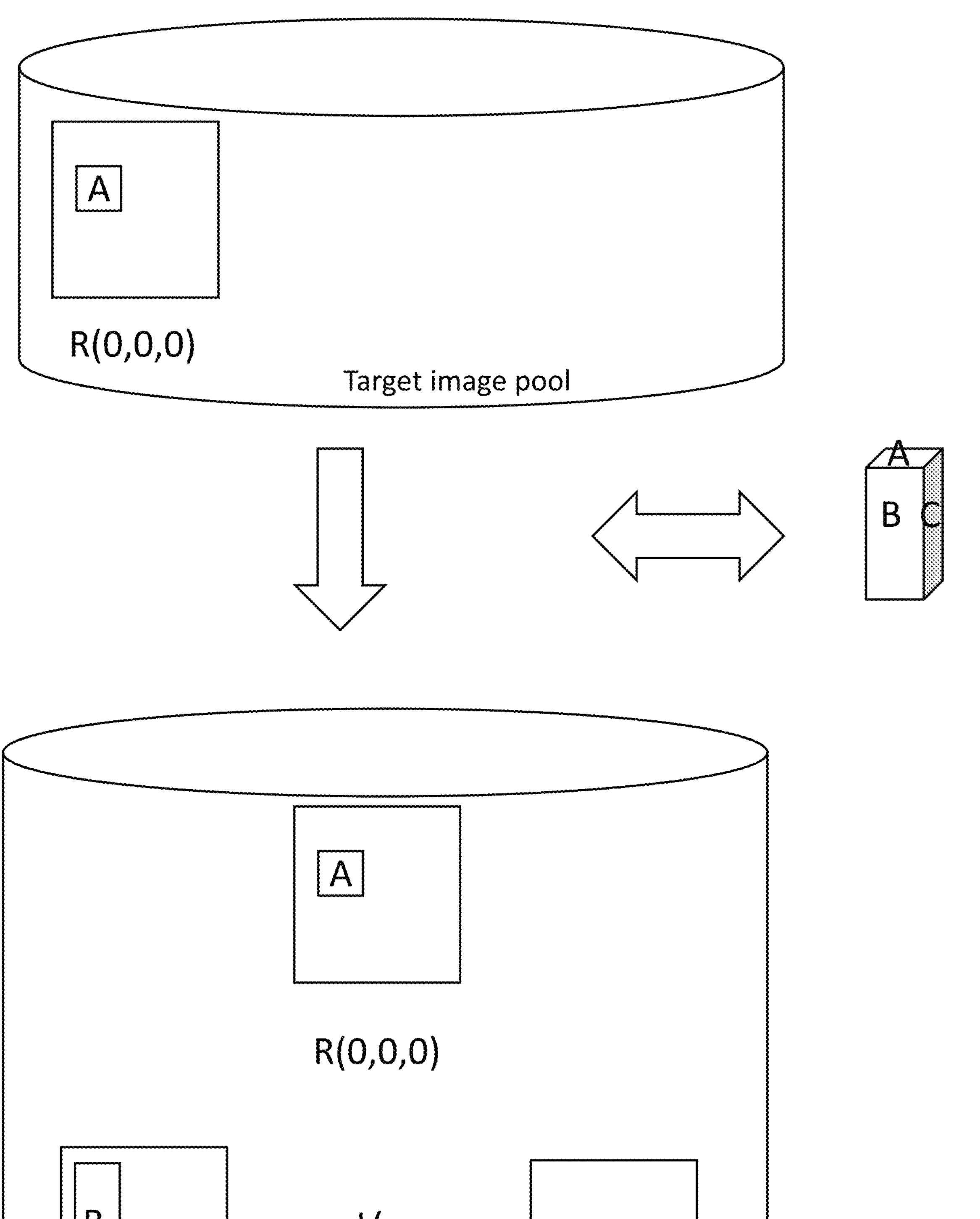
FIG. 4E illustrates a process of supplementing target training data for use in a medical image training process.

In addition to generating noise data to be combined with image data as described above, it is further possible to augment and/or replace training data used to train an untrained network when the training data is extracted from a training image volume (e.g., as constructed from acquired from a series of CT projections). FIG. 4D and FIG. 4E show a training image including an embedded three-dimensional feature (e.g., a stent) oriented within a three-dimensional object (e.g., a blood vessel) (depicted as a rectangular cube with three sides labeled "A", "B" and "C") that is contained within the training image volume. A first cross-sectional area of the embedded three-dimensional feature in the illustrated three-dimensional plane (e.g., corresponding to side "A") may be small as compared to other possible cross-sections that would be obtained from other three-dimensional planes (e.g., corresponding to sides "B" and "C"). The three-dimensional feature can be any feature desired to be included in the trained network like stents, bone, lesions, and reconstructive surgery implants. The more features included when training the network, the more robust the network will be.

As shown in FIG. 4D and FIG. 4E, a cross section of a stent (illustrated as a small square) included in an image representing an image slice along a first three-dimensional plane is included in an original set of training data. The cross section is illustrated as having a small cross sectional area in the first three-dimensional plane, and training a network to recognize it is increasingly difficult with decreasing cross sectional area. Accordingly, when the cross-section is selected as being a region of interest, either by a manual selection occurring after reviewing the training data or by an automated process of searching for embedded features, the location corresponding to the cross section is determined within the training image volume such that at least one alternate three-dimensional plane can be used to provide an image for training by adding it to the image pool and training it along with the original image or by replacing the original. As shown in FIG. 4D and FIG. 4E, the smaller cross section of a rectangular cube of side A has two other sides (labeled B and C) that have substantially larger cross sections that can be found by rotating the image volume with respect to the original angles. The original rotations that generated side A are considered to be 0 degrees in each of the X, Y, and Z directions and are represented by a rotational notation R(0, 0,0). To obtain an image of side B, the image volume is rotated in one direction 90 degrees as specified by the notation R(0,90,0). (A rotation in the first direction would rotate side A such that, for example, side A would be upside down when R(180,0,0), and such an image also may be added to the training data.) To obtain an image of side C, the image volume is rotated in the third direction 90 degrees as specified by the notation R(0,0,90). By using those orientations for training data, the system can better learn the image details of what would otherwise be image information that is more difficult to learn. While the above discussion has described using one or two alternate orientations for an embedded three-dimensional feature, including more orientations results in more learned data and higher quality images after training. For example, the reverse sides of sides B and C can be found by rotating in the opposite directions according to R(0,−90, 0) and R(0,0,−90), respectively. Furthermore, various other angles can be used, either alone or in combination such that angled viewed can be obtained (e.g., R(0, 45, 45), R(0, −45, 45), R(45, 45, 45), R(−45, 90, 180)). Additionally, other image modifications (e.g., translation T( ) and scaling S( )) can be used to produce additional training data, and the modifications can be applied together (e.g., S(R(T( ))) and T(S(R( ))).

FIG. 4D illustrates the replacement of the original image depicting the original cross section, A, with either or both new cross sections, B and C. FIG. 4E depicts adding either or both new images to the image pool with the original image.

Figure 4F:
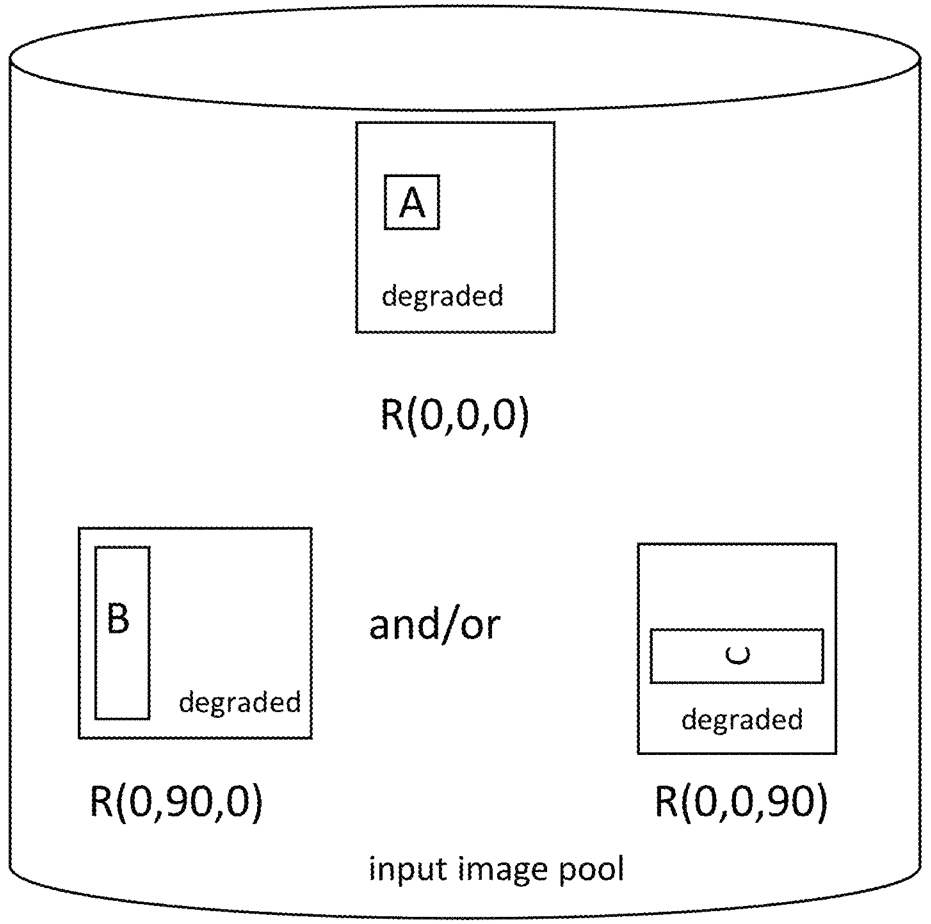
FIG. 4F illustrates a process of generating input training data from target training data for use in a medical image training process.

FIG. 4F illustrates that once a set of target images have been generated, their corresponding input images can be added to the input training data. Various techniques can be utilized to generate the input images to be paired with the target images. In one embodiment, target images are degraded (e.g., by being degraded according to a degradation function D( ) such as by adding synthetic noise). In an alternate embodiment, input images are created using a less accurate reconstruction technique as compared with corresponding target images. For example, the initial target images can have been reconstructed using iterative reconstruction whereas the corresponding input images are created using filtered backpropagation (FBP). The corresponding input and target image pairs can then be used to improve network robustness when training the network by training with the corresponding pairs {(D(A), A), (D(B), B), (D(C), C)} or using the rotational notation with respect to a particular feature {(D(R(0,0,0), R(0,0,0)), (D(R(0,90,0)),R (0,90,0)), D(R(0,0,90)),R(0,0,90))}.

Figure 4G:
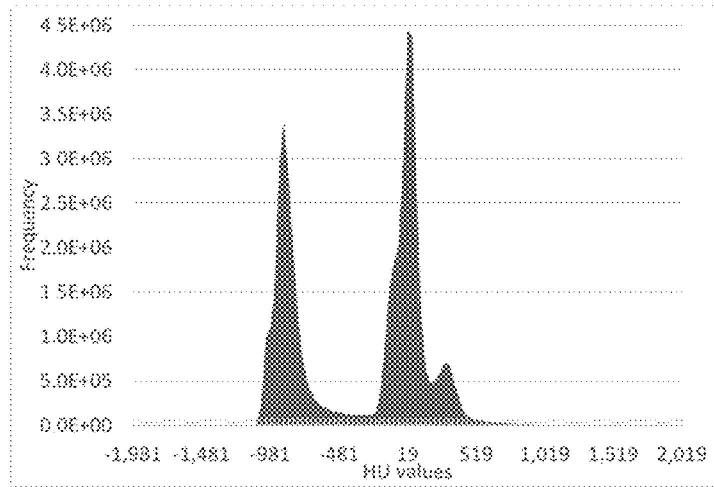
FIG. 4G illustrates a histogram of initial cardiac training data based on a Houndsfield units (HU) scale.
Figure 4H:
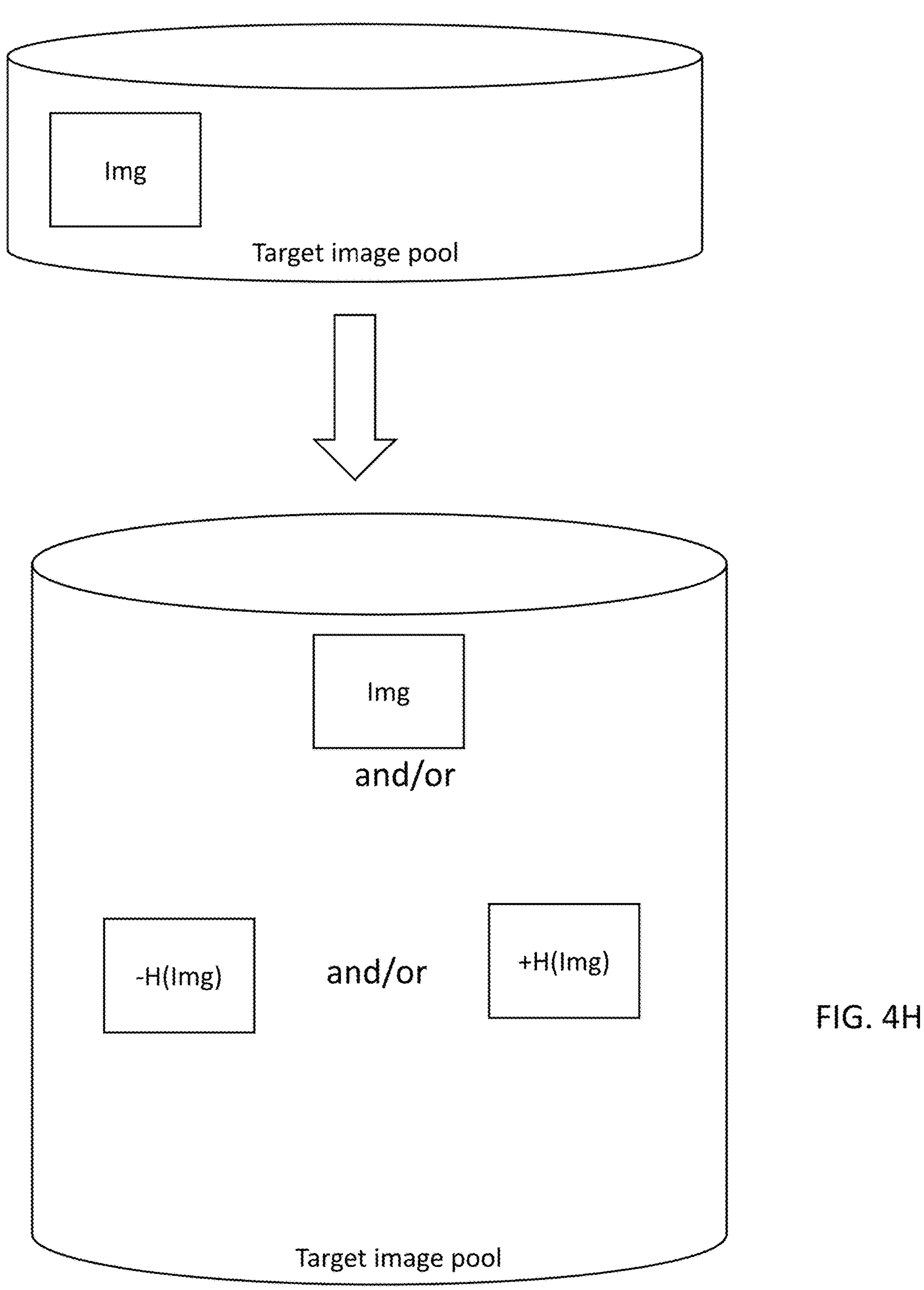
FIG. 4H illustrates training data including supplemented (cardiac) training data based on a Houndsfield units (HU) scale generated by HU shifting instead of or in addition to initial (cardiac) training data.

In addition to the other methods of providing additional training data described herein, it is further possible to augment and/or replace training data used to train an untrained network by shifting and/or scaling tissue density-related information (e.g., Houndsfield unit (HU) data) used in the training process. FIG. 4G illustrates a histogram of cardiac training data based on a Houndsfield units (HU) scale and indicates the density of tissue in the training data. FIG. 4G shows one histogram for an image slice in the cardiac region for a first patient. Although each image slice for the cardiac region can be different, the HU distribution generally is similar for the entire cardiac region for a single patient. However, different patients can have different HU ranges and distributions for the same region, so by scaling and or shifting HU distributions during training, the resulting trained network can be made more robust. HU values in CT images can cover different organs, contrast, and implanted metal. A typical range is from −1000 to 2000 or 3000 HUs. Known networks are trained and applied based on the anatomy since different anatomies have different image requirements, but the training data usually covers some specific ranges due to organ and contrast distribution. As described herein, training data with wider HU coverage and/or uniform HU distribution can improve the robustness of trained network. Furthermore, HU shift augmentation can extend HU coverage and make more uniform HU distribution.

Figure 4I:
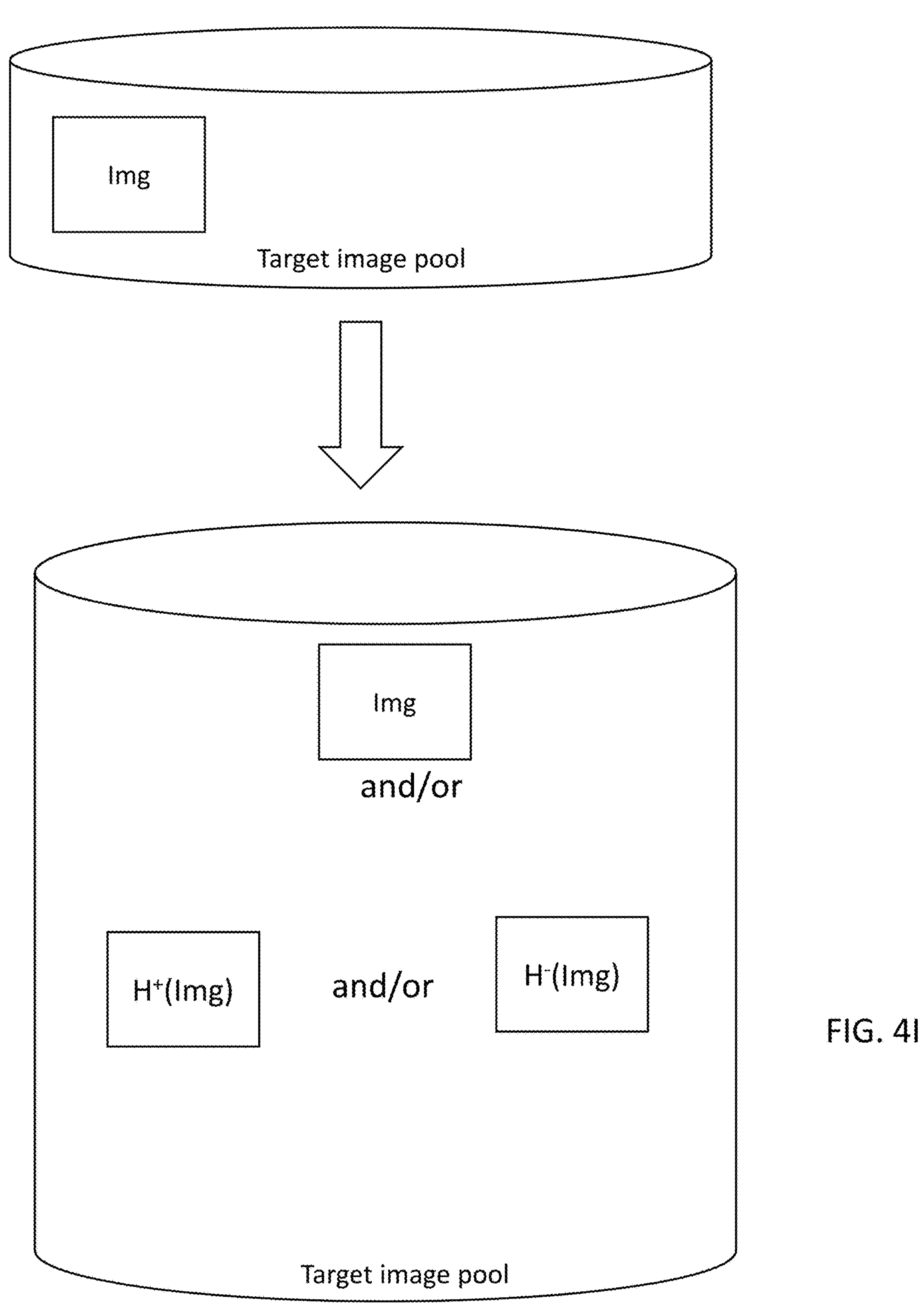
FIG. 4I illustrates training data including supplemented (cardiac) training data based on a Houndsfield units (HU) scale generated by HU scaling instead of or in addition to initial (cardiac) training data.

Similar to the process described above that supplements training data by adding various noise sources, training data can be supplemented by modifying HU data within an original training data set. For example, after receiving initial training data sets, the corresponding HU distribution can be obtained using the histogram method. The augmentation images $IMG_{aug}(x,y)$ can be generated to fill the gap between the peaks by $IMG_{aug}(x,y)=IMG(x,y)+val_{shift}$, and the process of such a shift will be referred to using the notation +H ( ). For shifts in an opposite direction, the shift process will be referred to as −H( ). Several values can be selected for $val_{shift}$ to produce images −H(img) and +H(img) to fill all the gaps in the HU range of [−1000, 2000] as shown in FIG. 4I.

When the training target images are from advanced reconstruction algorithms like iterative reconstruction, the reconstruction parameters can be optimized to improve the image quality of one or more specific regions. For example, high contrast region like bone usually get better spatial resolution improvement compared to low contrast region (typically soft tissue). The HU shift augmentation can benefit the image quality improvement of specific HU range from other HU ranges. For example, a cardiac scan can include additional features (e.g., liver and lungs) in the image depending upon the axial plane captured in the image. When the HU shift augmentation is applied to the image, the features of all three organs can be enhanced even though the HU distribution of liver and lungs are different from the initial cardiac HU distribution because the HU shift augmentation extends the covered range and makes the HU distribution more uniform.

In addition to the shifting process described above, the training data sets can be augmented/supplemented with images having scaled HU values. HU scaling augmentation can be realized by $IMG_{sca}(x,y)=val_{sca}*IMG(x,y)$. Several values (>1.0 or <1.0) can be selected for $val_{sca}$, and scaling with $val_{sca}>1.0$ will be referenced as $H^{+}(\ )$ and scaling with $val_{sca}<1.0$ will be referenced as $H^{-}(\ )$. One additional benefit of HU scaling is that the noise in the images is amplified or shrunk depending on the value of $val_{sca}$. The trained network with these additional noises at different levels is more robustness since more noise levels are covered during the training.

Figure 4J:
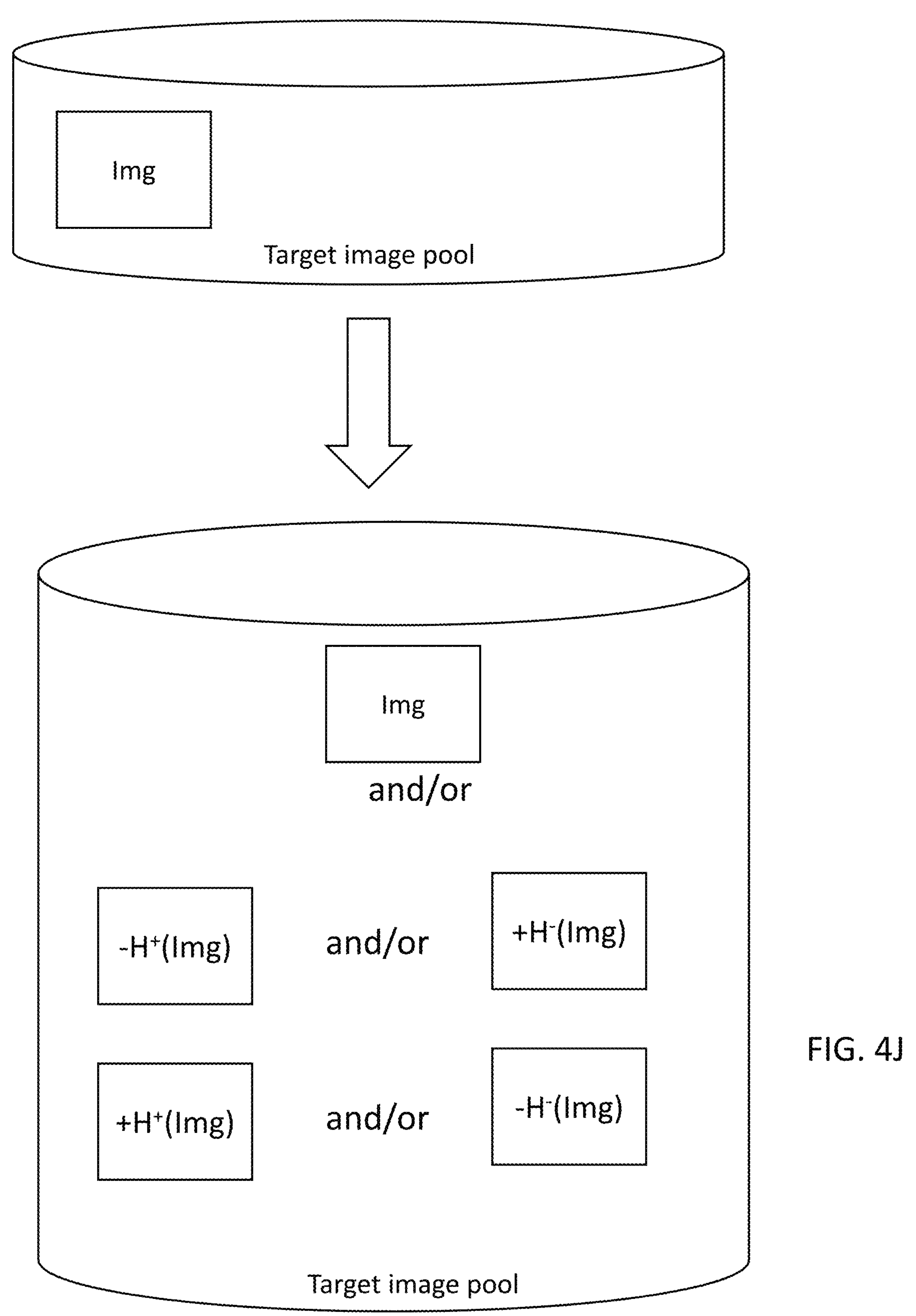
FIG. 4J illustrates training data including supplemented (cardiac) training data based on a Houndsfield units (HU) scale generated by HU scaling and shifting instead of or in addition to initial (cardiac) training data.

The trained network can be more robust by applying both HU shifting augmentation and HU scaling augmentation. FIG. 4J shows training data when both augmentations are applied. The advantage of applying both the HU shifting and HU scaling augmentations is providing training to the network with more uniform and extended HU coverage and amplified or reduced noise throughout the HU range. The HU shifting and HU scaling augmentations can be used in conjunction with image degradation (e.g., adding synthetic noise) to produce training pairs to improve network robustness when training the network. By including image degradation with the augmentation, the network can be trained to improve image features and image degradation simultaneously.

Figure 5A:
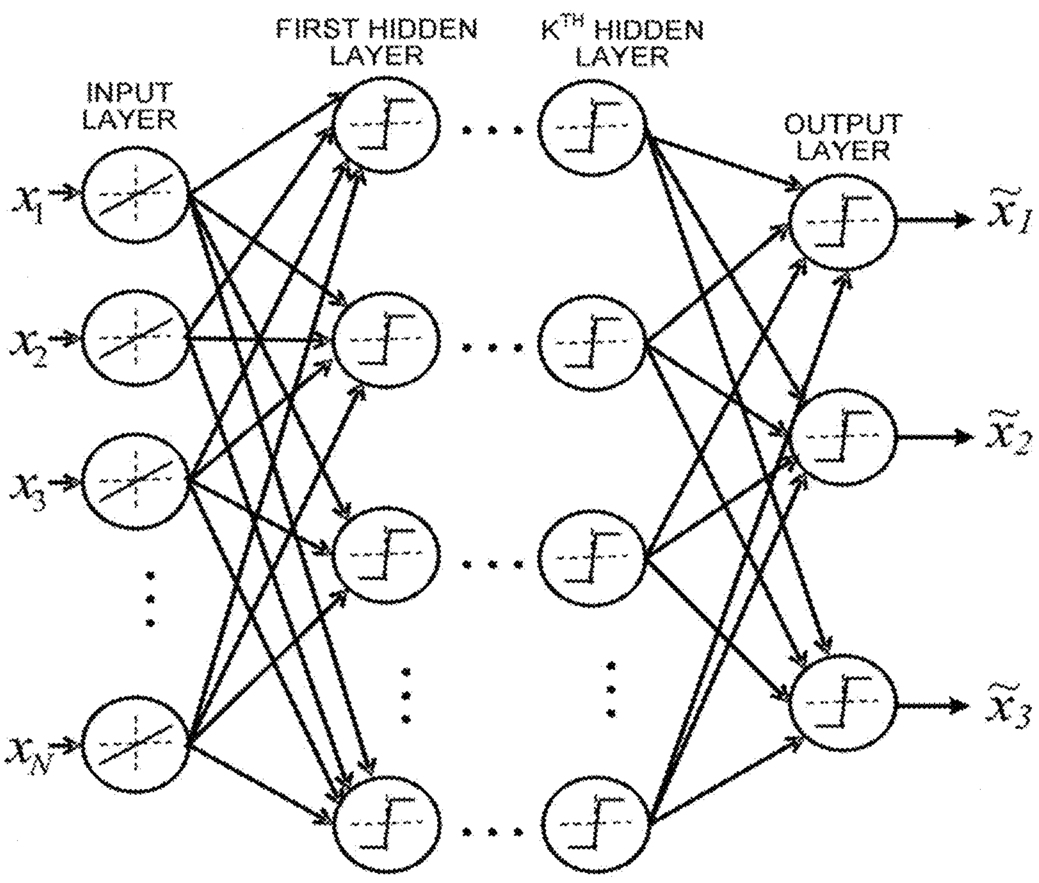
FIG. 5A illustrates a training process according to an exemplary embodiment described below.

Hereinafter, details of the training performed by the model generation function **144*d* will be described. FIG. 5A to FIG. 5**D illustrate a training process according to an exemplary embodiment described below.

More specifically, FIG. 5A illustrates a general artificial neural network (ANN) having n inputs, a $K^{th}$ hidden layer, and three outputs. Each layer of the ANN is made up of nodes (also called neurons), and each node performs a weighted sum of the inputs to produce an output and compares the result of the weighted sum with a threshold. ANNs make up a class of functions for which members of the class are acquired by varying thresholds, connection weights, or specifics of an architecture such as the number of nodes and/or their connectivity. The nodes in the ANN may be referred to as neurons (or neuronal nodes), and the neurons can have interconnections between different layers of the ANN system. For example, the ANN has more than three layers of neurons and has as many output neurons x to N as input neurons, wherein N is the number of pixels in the reconstructed image. Synapses (that is, connections between neurons) store values called "weights" (also interchangeably referred to as "coefficients" or "weighting coefficients") that manipulate data in calculations. The outputs of the ANN depend on three types of parameters: (i) An interconnection pattern between different layers of neurons, (ii) A learning process for updating weights of the interconnections, and (iii) An activation function that converts a neuron's weight input to its output activation.

Mathematically, a neuron's network function m(x) is defined as a composition $n_i$ (x) of other functions, which can further be defined as a composition of other functions. This can be conveniently represented as a network structure, with arrows depicting dependencies between variables, as illustrated in FIG. 5A. For example, the ANN can use a nonlinear weighted sum, wherein $m(x)=K(\Sigma_i w_i n_i(x))$, where K (commonly referred to as an "activation function") is a predetermined coefficient such as a sigmoidal function, a hyperbolic tangent function, and a rectified linear unit (ReLU).

In FIG. 5A (and similarly in FIG. 5B), the neurons (that is, nodes) are depicted by circles around a threshold function. In the non-limiting example illustrated in FIG. 5A, the inputs are depicted by circles around a linear function and the arrows indicate directed connections between neurons. In a specific embodiment, the ANN is a feedforward network as exemplified in FIG. 5A and FIG. 5B (for example, it can be represented as a directed acyclic graph).

The ANN operates to achieve a specific task, such as denoising of a CT image, by searching within the class of a function F to learn, using a set of observation results, to find an element $m^*(m^* \in F)$ which solves the specific task in some optical criteria (for example, stopping criteria used at step S260 to be described below). For example, in a specific embodiment, this can be achieved by defining a cost function C:F→R, such as for an optical solution expressed by the following Equation (1) (that is, no solution having a cost less than the cost of the optical solution).

Equation (1)

$$C(m^*) \leq C(m) \forall m \in F \tag{1}$$

In Equation (1), m* is the optical solution. The cost function C is a measure of how far away a particular solution is from an optical solution to a problem to be solved (for example, an error). Learning algorithms iteratively search through the solution space to fine a function with the smallest possible cost. In a specific embodiment, the cost is minimized over a sample of the data (that is, the training data).

Figure 5B:
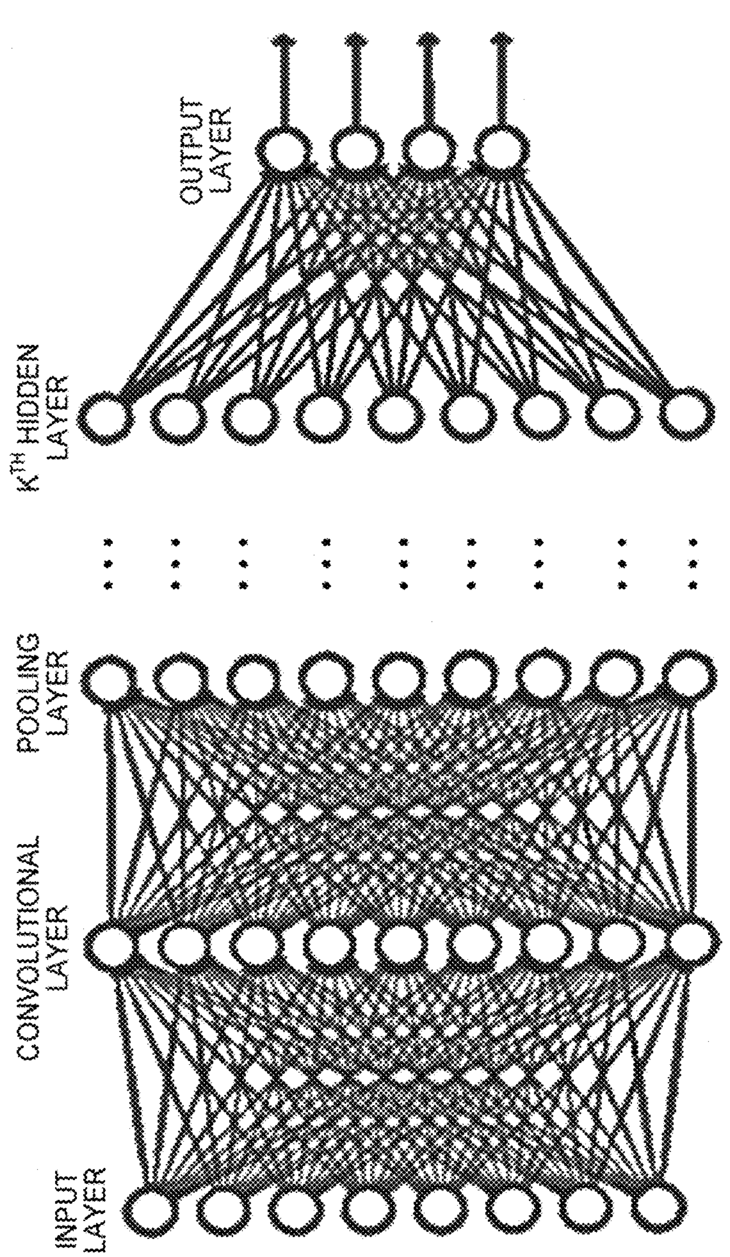
FIG. 5B illustrates a training process according to an exemplary embodiment described below.

FIG. 5B illustrates a non-limiting example in which the ANN is a DCNN. The DCNN is a type of ANN having beneficial properties for image processing, and, therefore, has a particular relevance for applications of image denoising. The DCNN uses a feedforward ANN in which a connectivity pattern between neurons can represent convolutions in image processing. For example, the DCNN can be used for image processing optimization by using multiple layers of small neuron collections that process portions of an input image, called receptive fields. The outputs of these collections can then be tiled so that they overlap, to achieve a better representation of the original image. This processing pattern can be repeated over multiple layers having alternating convolution and pooling layers. Note that FIG. 2B illustrates an example of a fully connected (full connect) network that defines a node of a succeeding layer by using all the nodes of a preceding layer. This example only illustrates an example of a deep neural network (DNN). It is common for the DCNN to form a loosely connected (partial connect) network that defines a node of a succeeding layer by using some of the nodes of a preceding layer.

FIG. 5C illustrates an example of a 5×5 kernel being applied to map values from an input layer representing a two-dimensional image to a first hidden layer which is a convolution layer. The kernel maps respective 5×5 pixel regions to corresponding neurons of the first hidden layer.

Following after the convolution layer, the DCNN can include local and/or global pooling layers that combine the outputs of neuron clusters in the convolution layers. Moreover, in a specific embodiment, the DCNN can also include various combinations of convolutional and fully connected layers, with pointwise nonlinearity applied at the end of or after each layer.

The DCNN has several advantages for image processing. To reduce the number of free parameters and improve generation, a convolution operation on small regions of input is introduced. One significant advantage of the specific embodiment of the DCNN is the use of shared weights in the convolution layer, that is, filters (weight banks) used as coefficients for each pixel in the layer are the same. Such significant advantages reduce a memory footprint and improve performance. Compared to other image processing methods, the DCNN advantageously uses relatively little pre-processing. This means that the DCNN is responsible for learning manually designed filters in traditional algorithms. The lack of dependence on prior knowledge and human effort in designing features is a major advantage for the DCNN.

In the DCNN, it is possible to utilize similarities between adjacent layers in reconstructed images. The signal in the adjacent layers is ordinarily highly correlated, whereas the noise is not. In general, a three-dimensional volumetric image in CT can provide more diagnostic information than a single slice that transverses a two-dimensional image because more volumetric features can be captured. FIG. 4C illustrates an exemplary training for denoising of a two-dimensional reconstructed image, but denoising that further uses volumetric characteristics may be trained.

Figure 5D:
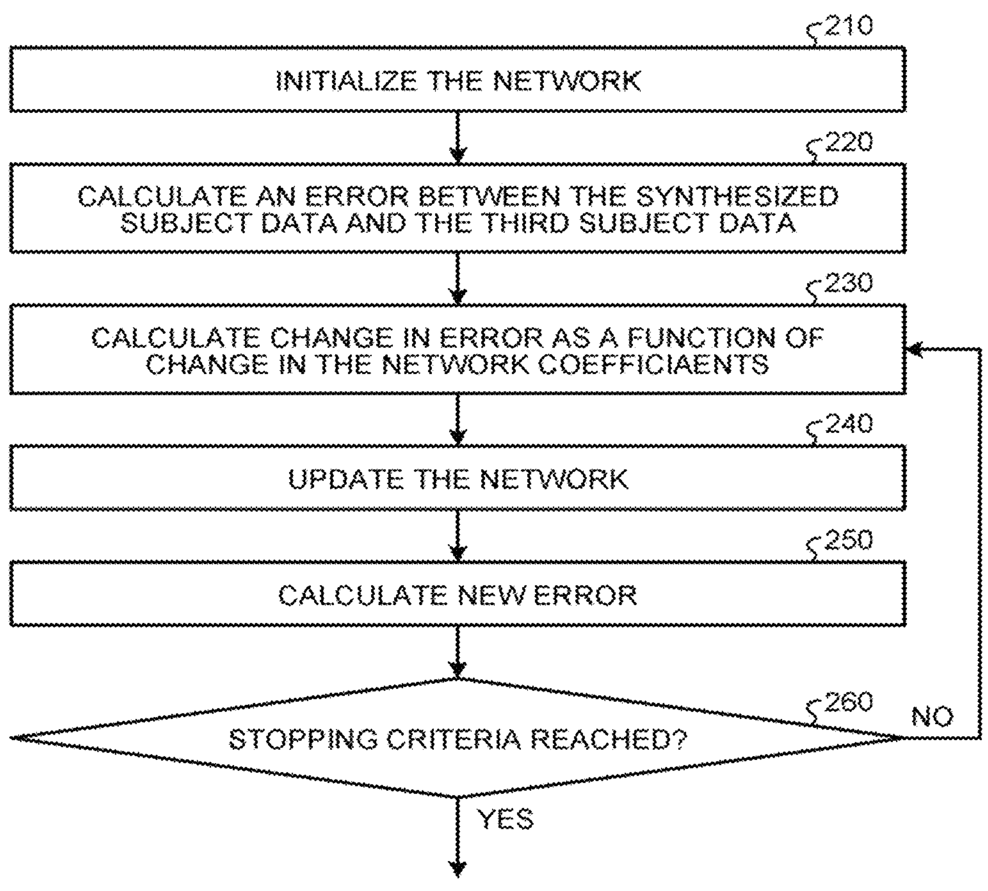
FIG. 5D illustrates a training process according to an exemplary embodiment described below.

FIG. 5D illustrates an exemplary embodiment of supervised learning used to train the DCNN. In the supervised learning, a set of training data is acquired, and the network is iteratively updated to reduce errors, such that the synthesized subject data processed by the DCNN closely matches the second subject projection data. In other words, the DCNN infers mapping implied by the training data, and the cost function produces an error value related to mismatch between the second subject projection data and denoised data produced by applying a current incarnation of the DCNN to the synthesized subject data. For example, in a specific embodiment, the cost function can use a mean-squared error to optimize an average squared error. In the case of multilayer perceptrons (MLP) neural network, a backpropagation algorithm can be used for training the network by minimizing the mean-squared-error-based cost function using a gradient descent method.

Training a neural network model essentially means selecting one model from the set of allowed models (or determining a distribution over the set of allowed models in a Bayesian framework) that minimize the cost criterion (that is, an error value calculated using the cost function). In general, DL networks can be trained using any of numerous algorithms for training neural network models (for example, applying optimization theory or statistical estimation).

For example, the optimization method used in training artificial neural networks can use some form of gradient descent, using backpropagation to compute actual gradients. This is done by taking the derivative of the cost function with respect to network parameters and then changing those parameters in a gradient-related direction. The backpropagation algorithm may be a steepest descent method (for example, with variable learning rate, with variable learning rate and momentum, and resilient backpropagation), a quasi-Newton method (for example, Broyden-Fletcher-Goldfarb-Shanno, one step secant, and Levenberg-Marquardt), or a conjugate gradient method (for example, Fletcher-Reeves update, Polak-Ribiére update, Powell-Beale restart, and scaled conjugate gradient). Moreover, evolutionary methods, such as gene expression programming, simulated annealing, expectation-maximization, non-parametric methods, and particle swarm optimization, can also be used for training the DCNN.

At step S210 of FIG. 5D, an initial guess is generated for the coefficients of the DCNN. For example, the initial guess may be based on a prior knowledge of a region being imaged or one or more denoising methods, edge detection methods, and/or blob detection methods. Moreover, the initial guess may be based on a DCNN trained on training data related to a different noise level or using a different CT scan method.

Exemplary denoising methods include linear smoothing filters, anisotropic diffusion, non-local means, or nonlinear filters. The linear smoothing filters remove noise by convolving the original image with a mask representing a low-pass filter or smoothing operation. For example, the Gaussian mask includes elements determined by a Gaussian function. This convolution brings the values of each pixel into closer to the values of pixels adjacent to the pixels. The anisotropic diffusion removes noise while preserving sharp boundaries by evolving an image under a smoothing partial differential equation similar to the heat conduction equation. A median filter is an example of a nonlinear filter and, when properly designed, the nonlinear filter can also preserve boundaries and avoid burring. The median filter is an example of a rank-conditioned rank-selection (RCRS) filter, which can be applied to remove salt and pepper noise from an image without introducing significant blurring artifacts. Moreover, a filter using a total-variation (TV) minimization regularization term can be used when an imaged region supports an assumption of uniformity over large areas demarked by sharp boundaries between uniform areas. The TV filter is another example of the nonlinear filter. In addition, non-local means filtering is an exemplary method of determining denoised pixels by using a weighted average over similar patches in an image.

At step S220 of FIG. 5D, an error (for example, a cost function) is calculated between the network processed synthesized subject data and the second subject projection data. The error can be calculated using any known cost function or distance measure between image data, including those cost functions described above.

At step S230 of FIG. 5D, a change in the error can be calculated as a function of a change in the network (for example, an error gradient), and this change in the error can be used to select a direction and step size for a subsequent change to the weights/coefficients of the DCNN. Calculating the gradient of the error in this manner is consistent with specific embodiments of a gradient descent optimization method. In other specific embodiments, as would be understood by a person skilled in the art, this step may be omitted and/or replaced with another step in accordance with another optimization algorithm (for example, a non-gradient descent optimization algorithm like simulated annealing or a genetic algorithm).

At step S240 of FIG. 5D, a new set of coefficients are determined for the DCNN. For example, the weights/coefficients can be updated using the change calculated at step S230, as in a gradient descent optimization method or an over-relaxation acceleration method.

At step S250 of FIG. 5D, a new error value is calculated using the updated weights/coefficients of the DCNN.

At step S260 of FIG. 5D, predetermined stopping criteria are used to determine whether the training of the network is complete. For example, the predetermined stopping criteria can determine whether the new error and/or the total number of iterations performed exceeds a threshold. For example, the stopping criteria can be satisfied when the new error falls below a predetermined threshold or a maximum number of iterations is reached. When the stopping criteria are not satisfied, the procedure returns to step S230 to repeat the process, that is, the procedure will be continued back to the start of the iterative loop by using the new weights/coefficients (the iterative loop includes steps S230, S240, S250, and S260). When the stopping criteria are satisfied, the training of the DCNN is completed.

In addition to the embodiment for error minimization illustrated in FIG. 5D, the training of the DCNN can use one of many other known minimization methods including, for example, local minimization methods, convex optimization methods, and global optimization methods.

When the cost function (for example, the error) has a local minimum different from the global minimum, a robust stochastic optimization process is beneficial to find the global minimum of the cost function. An example of an optimization method for finding a local minimum can be a Nelder-Mead simplex method, a gradient descent method, a Newton's method, a conjugate gradient method, a shooting method, and one of other known local optimization methods. There are also many known methods for finding global minima, including generic algorithms, simulated annealing, exhaustive searches, interval methods, and other related deterministic, stochastic, heuristic, and metaheuristic method. Any of these methods can be used to optimize the weights/coefficients of the DCNN. Moreover, neural networks can also be optimized using a backpropagation method.

For example, the model generation function 144*d* performs residual learning an input of which is the synthesized subject data and a target of which is the second subject projection data. In the residual learning, a difference between input data including noise and target data is learned. In the case of a clinically obtained noise image, noise included in the image have a statistical dependency on an image signal, but noise added to the synthesized subject data do not have such dependency. However, in the residual learning, the difference between the input data and the target data and characteristics of the noise itself are more important factors than the dependency of the noise on the image signal. Accordingly, the model generation function 144*d* can train the DCNN with the same degree of accuracy as when the synthesized subject data is input and the clinically obtained noise image is input.

Here, the second subject projection data may be noisy data or clean data. That is, the model generation function 144*d* may perform noise-to-noise training or noise-to-clean training for the DCNN.

For example, the projection data Yk−1, the projection data Yk, and the projection data Yk+1 illustrated in FIG. 4B may be projection data imaged using a low dose of X-rays. That is, the first subject projection data and the second subject projection data may be data obtained with low-dose imaging. Furthermore, for example, the acquisition function 144*c* may also acquire the second subject projection data by using a reconstruction method other than a highly accurate reconstruction method such as the successive approximation reconstruction method. As an example, the acquisition function 144*c* performs the FBP as the reconstruction processing R2 illustrated in FIG. 4B. With this, the acquisition function 144*c* sets the second subject projection data stored in the image pool 141*c* as noisy data. In such a case, since noise included in the second subject projection data and noise based on the noise data added to the synthesized subject data are independent, the model generation function 144*d* can perform the noise-to-noise training to acquire a DCNN.

Furthermore, for example, the acquisition function 144*c* acquires the first subject projection data by performing the reconstruction processing based on a first reconstruction method and acquires the second subject projection data by performing the reconstruction processing based on a second reconstruction method with higher accuracy than the first reconstruction method. As an example, the acquisition function 144*c* performs the FBP as the reconstruction processing R1 illustrated in FIG. 4B, and performs the successive approximation reconstruction method as the reconstruction processing R2. With this, the acquisition function 144*c* can use the second subject projection data stored in the image pool 141*c* as clean data, and the model generation function 144*d* can perform the noise-to-clean training to acquire a DCNN. Note that the DCNN in such a case performs training an input of which is an image based on the FBP method and a target of which is an image based on the successive approximation reconstruction method. That is, the DCNN can learn a difference depending on the reconstruction method. Accordingly, the model generation function 144*d* can function the DCNN to reduce noise in the input data and improve the resolution.

The model generation function 144*d* may generate a DCNN for each part such as the lung, abdomen, and pelvis. For example, the model generation function 144*d* may perform training by using data of the lung as the synthesized subject data or the second subject projection data, thereby obtaining a DCNN. The DCNN in such a case is a learned model specialized for the noise reduction processing of an image obtained by imaging the lung.

Alternatively, the model generation function 144*d* may perform training by using data of various parts as the synthesized subject data or the second subject projection data, thereby obtaining a DCNN. The DCNN in such a case is a general-purpose learned model that receives the input of an image obtained by imaging an arbitrary part and performs the noise reduction processing.

Furthermore, the model generation function 144*d* may generate a DCNN for each noise level. For example, the acquisition function 144*c* acquires noise data based on the data acquired from a subject for noise generation imaged at a predetermined dose, and generates the noise pool 141*a*. Furthermore, for example, the acquisition function 144*c* adjusts the value of a parameter $\alpha$ such that the noise level has a predetermined value, and generates the noise pool 141*a*. Furthermore, the model generation function 144*d* acquires the synthesized subject data based on the noise data read from the noise pool 141*a* and the first subject projection data. With this, the model generation function 144*d* can allow the noise level of the noise added to the synthesized subject data to be substantially constant. Then, the model generation function 144*d* performs training by using the synthesized subject data and the second subject projection data, thereby acquiring a DCNN. The DCNN in such a case is a learned model specialized for the noise reduction processing of an image obtained by imaging at a predetermined dose.

Alternatively, the model generation function 144*d* may perform training by using synthesized subject data of various noise levels, thereby obtaining a DCNN. The DCNN in such a case is a general-purpose learned model that receives the input of an image obtained by imaging at an arbitrary dose and performs the noise reduction processing.

Furthermore, the model generation function 144*d* may generate a DCNN for each image size. For example, the model generation function 144*d* may perform training by using the synthesized subject data or the second subject projection data cut in a predetermined size, thereby obtaining a DCNN. Alternatively, the model generation function 144*d* may perform training by using the synthesized subject data or the second subject projection data having various image sizes, thereby obtaining a DCNN.

As described above, the model generation function 144*d* acquires a DCNN by machine learning using the synthesized subject data and the second subject projection data, and allows the learned DCNN to be stored in the memory 141. Thereafter, for example, when input subject data is obtained by imaging a subject P12, the noise reduction processing function 144*e* can perform the noise reduction process of the input subject data by using the DCNN read from the memory 141. Note that the subject P12 may be a subject different from the projection data Yk−1, the projection data Yk, and the projection data Yk+1 illustrated in FIG. 4A and the projection data Yl−1, the projection data Yl, and the projection data Yl+1 illustrated in FIG. 4B, or may be the same subject. The subject P12 is an example of the subject P1.

Specifically, the imaging function 144*b* images the subject P12 and acquires projection data. Furthermore, the noise reduction processing function 144*e* performs the reconstruction processing based on the FBP method and generates a reconstructed image. The reconstructed image is an example of the input subject data. Next, the noise reduction processing function 144*e* reduces noise in the reconstructed image by the DCNN read from the memory 141, thereby obtaining denoised data.

Figure 6A:
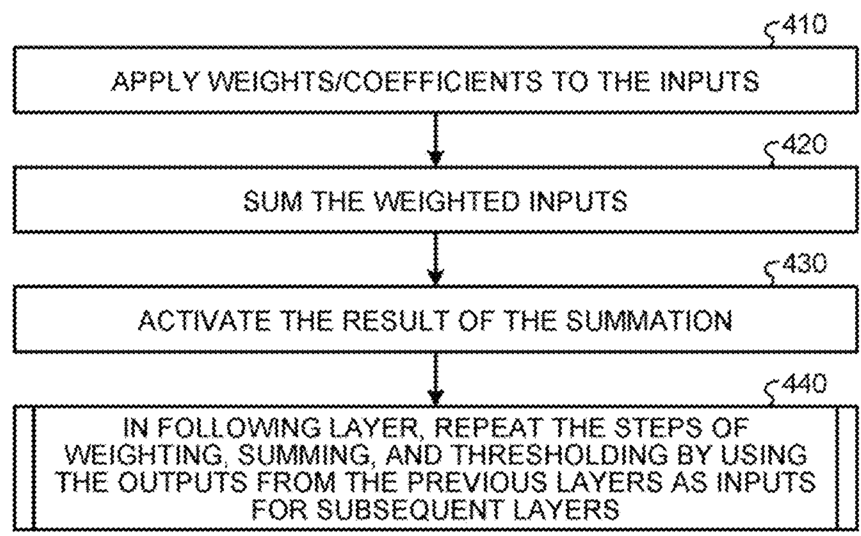
FIG. 6A illustrates a noise reduction process according to an exemplary embodiment described below.
Figure 6B:
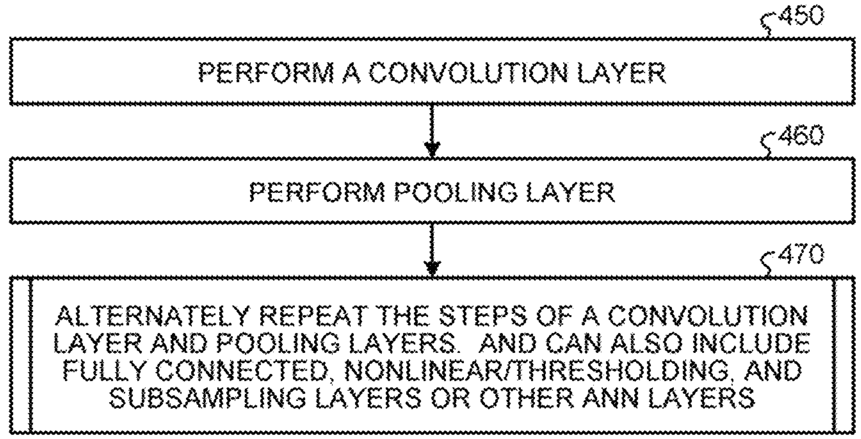
FIG. 6B illustrates a noise reduction process according to an exemplary embodiment described below.

Hereinafter, a noise reduction process using the DCNN will be described in detail. FIG. 6A and FIG. 6B illustrate the noise reduction process according to a first embodiment.

FIG. 6A is general for all ANNs and FIG. 6B is particular to CNNs. A series of processes in FIG. 6A corresponds to applying the DCNN to the input subject data. Following after a convolution layer, the DCNN can include local and/or global pooling layers, which combine the outputs of neuron clusters in the convolution layers.

At step S410, the weights/coefficients corresponding to the connections between neurons (that is, nodes) are applied to the respective inputs corresponding to the pixels of the reconstructed image.

At step S420, the weighted inputs are summed. When only non-zero weights/coefficients connecting to a predetermined neuron on the next layer are regionally localized in an image represented in the previous layer, the combination of steps S410 and S420 is essentially identical to performing a convolution operation.

At step S430, respective thresholds are applied to the weighted sums of the respective neurons.

At step S440, the steps of weighting, summing, and activating are repeated for each of the subsequent layers.

FIG. 6B illustrates a flow schematic diagram of another embodiment of the noise reduction process using the DCNN. The embodiment of step S170 illustrated in FIG. 6B corresponds to an operation on the reconstructed image using a non-limiting embodiment of a CNN for the DCNN.

At step S450, calculations for a convolution layer are performed as described above according to the understanding of a person skilled in the art in convolution layers.

At step S460, the outputs from the convolution layer are the inputs into a pooling layer. The pooling layer is performed according to the aforementioned description of pooling layers and is performed according to the understanding of a person skilled in the art in pooling layers.

At step S470, the steps of a convolution layer followed by a poling layer can be repeated a predetermined number of layers. Following (or intermixed with) the mixed convolution and poling layers, the output from a poling layer can be fed to a predetermined number of ANN layers performed according to the description provided for the ANN layers in FIG. 6A. The final output will be a desired reconstructed image (denoised data) characterized by no noise/artifact.

Then, the output function 144*f* outputs an image of the subject P12 based on the denoised data. For example, the output function 144*f* generates a display image based on the denoised data and allows the display 142 to display the display image. Alternatively, the output function 144*f* may transmit the image of the subject P12 based on the denoised data to an external device such as a workstation.

Figure 7:
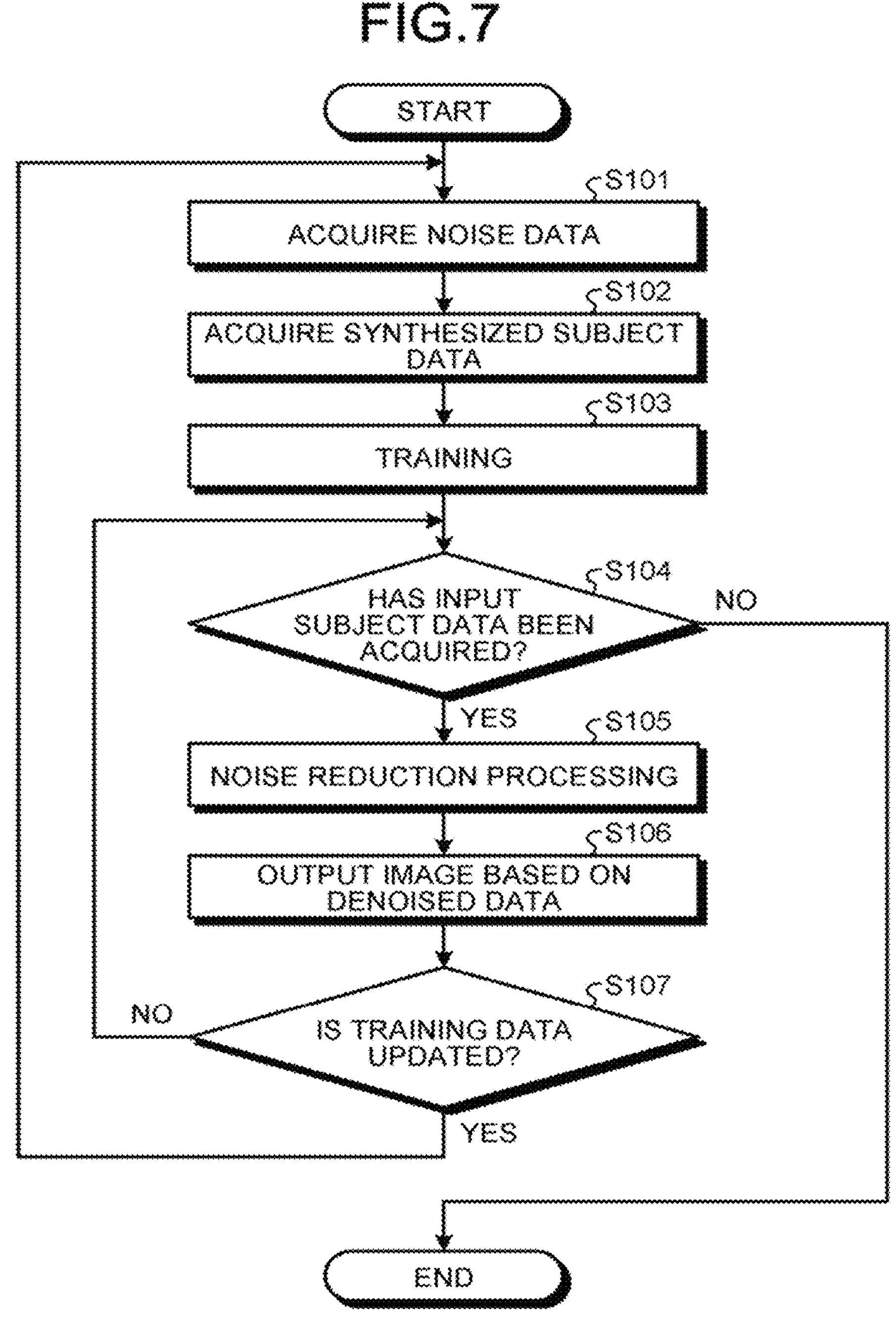
FIG. 7 illustrates a process of an X-ray CT apparatus according to an exemplary embodiment described below.

Next, an example of the processing procedure by the X-ray CT apparatus 10 will be described with reference to FIG. 7. FIG. 7 is a flowchart for explaining a series of flows of the process of the X-ray CT apparatus 10 according to the first embodiment. Step S101, step S102, and step S107 correspond to the acquisition function 144*c*. step S103 corresponds to the model generation function 144*d*. step S104 and step S105 correspond to the noise reduction processing function 144*e*. Step S106 corresponds to the output function 144*f*.

First, the processing circuitry 144 acquires the noise data based on the data acquired from a subject for noise generation (step S101), and acquires the synthesized subject data based on the first subject projection data and the noise data (step S102). Next, the processing circuitry 144 acquires the noise reduction processing model such as the DCNN by the machine learning using the synthesized subject data and the second subject projection data (step S103).

Next, the processing circuitry 144 determines whether the input subject data obtained by imaging the subject P12 has been acquired (step S104). When the input subject data has been acquired (Yes at step S104), the processing circuitry 144 reduces noise in the input subject data by the noise reduction processing model to acquire denoised data (step S105). Furthermore, the processing circuitry 144 outputs the image of the subject P12 based on the denoised data (step S106).

Here, the processing circuitry 144 determines whether to update training data (step S107). When updating the training data (Yes at step S107), the processing circuitry 144 proceeds to step S101 again. That is, when updating the training data, the processing circuitry 144 sets data obtained by imaging the subject P12 as the data acquired from a subject for noise generation, acquires the noise data in the data acquired from a subject for noise generation, and adds the noise data to the noise pool 141*a*. Alternatively, the processing circuitry 144 may set the data obtained by imaging the subject P12 as the first subject projection data or the second subject projection data, and add the first subject projection data or the second subject projection data to the image pool 141*b* or the image pool 141*c*. On the other hand, when not updating the training data (No at step S107), the processing circuitry 144 proceeds to step S104 again. Furthermore, when the input subject data is not acquired at step S104 (No at step S104), the processing circuitry 144 ends the process.

As described above, according to the first embodiment, based on the data acquired from a subject for noise generation obtained by the imaging performed by the X-ray CT apparatus 10, the acquisition function 144*c* acquires the noise data in the data acquired from a subject for noise generation. Furthermore, based on the first subject projection data and the noise data acquired by the imaging performed by a same kind of medical image diagnostic modality (X-ray CT) as the X-ray CT apparatus 10, the acquisition function 144*c* acquires the synthetic subject data in which noise based on the noise data are added to the first subject projection data. Furthermore, the model generation function 144*d* acquires the noise reduction processing model by machine learning using the synthetic subject data and the second subject projection data acquired by the imaging performed by the X-ray CT. With this, the X-ray CT apparatus 10 according to the first embodiment can easily acquire a high-quality noise reduction processing model.

For example, the data acquired from a subject for noise generation, the first subject projection data, and the second subject projection data described above do not need to be clean data acquired using a high dose of X-rays, and can be acquired relatively easily. Furthermore, since the synthesized subject data is acquired by combining the noise data and the first subject projection data, it is easy to prepare a required number of data for training. Accordingly, the X-ray CT apparatus 10 can easily prepare training data and improve the quality of the noise reduction processing model with sufficient training data.

Furthermore, when the noise reduction processing model is generated using noise generated by the simulation as the training data, the quality of the noise reduction processing model also changes according to the accuracy of the noise simulation. On the other hand, the noise in the aforementioned noise data are not simulated, but are extracted from the clinically obtained data acquired from a subject for noise generation. That is, the X-ray CT apparatus 10 can generate the noise reduction processing model by using more reliable training data and improve the performance of the noise reduction processing.

So far, although the first embodiment has been described, it may be implemented in various different forms other than the aforementioned embodiment.

For example, in FIG. 3A, it has been described that the projection data Y1 is sampled to acquire two pieces of projection data (the projection data Y11 and the projection data Y12). However, the embodiment is not limited thereto. For example, the acquisition function 144*c* may acquire three or more pieces of projection data by sampling the projection data Y1.

As an example, by sampling the projection data Y1, the acquisition function 144*c* acquires "3n (n is a natural number)" views in the projection data Y1 as the projection data Y11, acquires "3(n+1)" views in the projection data Y1 as the projection data Y12, and acquires "3(n+2)" views in the projection data Y1 as projection data Y13. Furthermore, the acquisition function 144*c* reconstructs the reconstructed image X11 from the projection data Y11, reconstructs the reconstructed image X12 from the projection data Y12, and reconstructs a reconstructed image X13 from the projection data Y13.

Then, the acquisition function 144*c* performs noise extraction processing based on the reconstructed image X11, the reconstructed image X12, and the reconstructed image X13. For example, the acquisition function 144*c* acquires noise data by performing difference processing between the reconstructed image X11 and the reconstructed image X12. Furthermore, the acquisition function 144*c* acquires noise data by performing difference processing between the reconstructed image X12 and the reconstructed image X13. Furthermore, the acquisition function 144*c* acquires noise data by performing difference processing between the reconstructed image X13 and the reconstructed image X11.

Furthermore, in FIG. 3A, the case has been described in which a plurality of reconstructed images are generated and noise data is extracted by performing difference processing between images. However, the extraction method of the noise data is not limited thereto. For example, the acquisition function 24*b* may omit the sampling, generate the reconstructed images based on the projection data Y1, and extract the noise data by performing image processing on the reconstructed images.

Furthermore, in FIG. 4B, it has been described that the first subject projection data to be stored in the image pool 141*b* and the second subject projection data to be stored in the image pool 141*c* are respectively generated by performing the reconstruction processing R1 and the reconstruction processing R2. However, the embodiment is not limited thereto. For example, the acquisition function 144*c* may allow data based on a first subset of the projection data such as the projection data Yl−1, the projection data Yl, and the projection data Yl+1 to be stored in the image pool 141*b* as the first subject projection data and allow data based on a second subset different from the first subset to be stored in the image pool 141*c* as the second subject projection data. In other words, based on subject data of a certain subject, the acquisition function 144*c* may generate first subject projection data corresponding to a first subset of the subject data and second subject projection data corresponding to a second subset different from the first subset.

As an example, the acquisition function 144*c* acquires the first subset by sampling odd view data in the projection data Yl−1, and allows a reconstructed image based on the first subset to be stored in the image pool 141*b* as the first subject projection data. Furthermore, the acquisition function 144*c* acquires the second subset by sampling even view data in the projection data Yl−1, and allows a reconstructed image based on the second subset to be stored in the image pool 141*c* as the second subject projection data. Although the case where the sampling is performed separately for the odd view data and the even view data, the sampling method can be arbitrarily changed.

Furthermore, in FIG. 4B, it has been described that the first subject projection data and the second subject projection data are generated from the same projection data. However, the embodiment is not limited thereto. For example, the acquisition function 144*c* may generate only the first subject projection data based on the projection data Yl−1, and may generate only the second subject projection data based on the projection data Yl. That is, the image pool 141*b* and the image pool 141*c* may be generated from different pieces of projection data.

Furthermore, in the aforementioned embodiment, although the first subject projection data and the second subject projection data have been described as different pieces of data, the first subject projection data and the second subject projection data may be the same data. For example, the acquisition function 144*c* acquires the synthesized subject data based on the noise data stored in the noise pool 141*a* and the data stored in the image pool 141*b*. Then, the model generation function 144*d* can obtain a DCNN by performing training using the synthesized subject data and the data stored in the image pool 141*b*.

Furthermore, in the aforementioned embodiment, the DCNN, which receives the input of the reconstructed image and performs the noise reduction processing, has been described as an example of the noise reduction processing model. However, the embodiment is not limited thereto. For example, the model generation function 144*d* may generate, as the noise reduction processing model, a DCNN that receives the input of projection data such as a sinogram and performs the noise reduction processing.

For example, similarly to the case illustrated in FIG. 4A, the acquisition function 144*c* first performs noise extraction processing on each of the projection data such as the projection data Yk−1, the projection data Yk, and the projection data Yk+1, thereby generating volume data indicating a noise distribution. Next, the acquisition function 144*c* generates forward projection data in which the volume data indicating the noise distribution has been forward projected for each of a plurality of views. Such forward projection data is, for example, a sinogram indicating the noise distribution. Furthermore, such forward projection data is an example of the noise data in the data acquired from a subject for noise generation. In other words, the noise data may be data indicating noise intensity at each position in the projection data space. The acquisition function 144*c* generates a plurality of forward projection data, which are the noise data, and allows the forward projection data to be stored in the noise pool 141*a*.

Furthermore, similarly to the case illustrated in FIG. 4B, the acquisition function 144*c* generates a reconstructed image by performing the reconstruction processing R1 on each of the projection data such as the projection data Yl−1, the projection data Yl, and the projection data Yl+1. Next, the acquisition function 144*c* generates forward projection data in which the generated reconstructed image has been forward projected for each of a plurality of views. Such forward projection data is, for example, a sinogram having a quality according to the reconstruction processing R1. Furthermore, such forward projection data is an example of the first subject projection data. The acquisition function 144*c* generates a plurality of forward projection data, which are the first subject projection data, and allows the forward projection data to be stored in the image pool 141*b*.

Furthermore, similarly to the case illustrated in FIG. 4B, the acquisition function 144*c* generates a reconstructed image by performing the reconstruction processing R2 on each of the projection data such as the projection data Yl−1, the projection data Yl, and the projection data Yl+1. Next, the acquisition function 144*c* generates forward projection data in which the generated reconstructed image has been forward projected for each of a plurality of views. Such forward projection data is, for example, a sinogram having a quality according to the reconstruction processing R2. Furthermore, such forward projection data is an example of the second subject projection data. The acquisition function 144*c* generates a plurality of forward projection data, which are the second subject projection data, and allows the forward projection data to be stored in the image pool 141*c*.

Next, the acquisition function 144*c* acquires the synthesized subject data based on the noise data read from the noise pool 141*a* and the first subject projection data read from the image pool 141*b*. Such synthesized subject data is, for example, a sinogram to which noise based on the noise data have been added. Then, the model generation function 144*d* obtains a DCNN by training a model by deep learning an input of which is the synthesized subject data and a target of which is the second subject projection data. The DCNN in such a case is functionalized to receive the input of projection data obtained by imaging the subject P12, for example, and to reduce noise in the projection data. Note that the projection data obtained by imaging the subject P12 is an example of input subject data.

For example, the imaging function 144*b* acquires the projection data by imaging the subject P12. Furthermore, the noise reduction processing function 144*e* reduces noise in the projection data by the DCNN and obtain denoised data. Then, the output function 144*f* outputs the image of the subject P12 based on the denoised data. For example, the output function 144*f* performs reconstruction processing on the denoised data and generates a reconstructed image. Moreover, the output function 144*f* generates a display image based on the reconstructed image and allows the display 142 to display the display image. Alternatively, the output function 144*f* may transmit the reconstructed image and the display image to an external device such as a workstation.

Furthermore, in the aforementioned embodiment, the noise reduction processing model has been described as being configured by the DCNN. However, the embodiment is not limited thereto. For example, the noise reduction processing function 144*e* may configure the noise reduction processing model by another type of neural network such as a fully connected neural network and a recurrent neural network (RNN). Furthermore, the noise reduction processing function 144*e* may generate the noise reduction processing model by a machine learning method other than the neural network. For example, the noise reduction processing function 144*e* may generate the noise reduction processing model by performing machine learning using an algorithm such as logistic regression analysis, nonlinear discriminant analysis, support vector machine (SVM), random forest, and naive Bayes.

Furthermore, in the aforementioned embodiment, the X-ray CT has been described as an example of the medical image diagnostic modality. However, the embodiment is not limited thereto, and similar processing can also be performed on information acquired by imaging performed by another medical image diagnostic modality. For example, the aforementioned embodiment can also be similarly applied to information acquired by imaging performed by an X-ray diagnostic apparatus, magnetic resonance imaging (MRI), ultrasonic imaging, and imaging performed by a single photon emission computed tomography (SPECT), a positron emission computed tomography (PET), and the like.

Furthermore, in the aforementioned embodiment, the case has been described in which the processing circuitry 144 in the X-ray CT apparatus 10 performs various functions such as the acquisition function 144*c*, the model generation function 144*d*, the noise reduction processing function 144*e*, and the output function 144*f*. However, the embodiment is not limited thereto. For example, processing circuitry included in an apparatus different from the X-ray CT apparatus 10 may perform functions corresponding to the respective functions of the processing circuitry 144.

Figure 8:
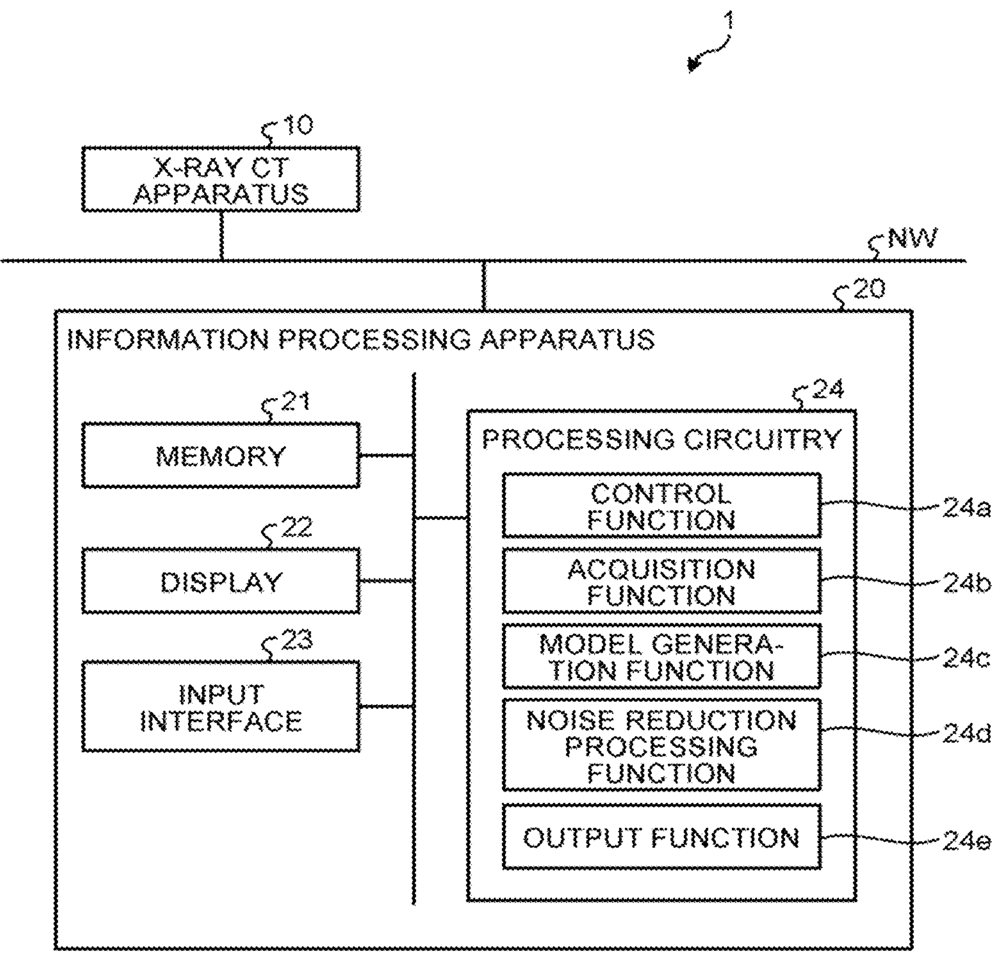
FIG. 8 is a block diagram of an exemplary configuration of an X-ray CT apparatus according to another exemplary embodiment described below.

Hereinafter, this point will be described with reference to FIG. 8. FIG. 8 is a block diagram illustrating an example of a configuration of an information processing system 1 according to a second embodiment. For example, the information processing system 1 includes an X-ray CT apparatus 10 and an information processing apparatus 20 as illustrated in FIG. 8. The X-ray CT apparatus 10 and the information processing apparatus 20 are connected to each other via a network NW.

Note that the location where the X-ray CT apparatus 10 and the information processing apparatus 20 are installed is arbitrary as long as they can be connected via the network NW. For example, the X-ray CT apparatus 10 and the information processing apparatus 20 may be installed within facilities different from each other. That is, the network NW may be a local network closed within the facility or a network via the Internet. Furthermore, communication between the X-ray CT apparatus 10 and the information processing apparatus 20 may be performed via another apparatus such as an image storage apparatus, or may be directly performed without using another apparatus. An example of such an image storage apparatus includes a picture archiving and communication system (PACS) server, for example.

The X-ray CT apparatus 10 illustrated in FIG. 8 has the same configuration as that of the X-ray CT apparatus 10 illustrated in FIG. 1A. However, the processing circuitry 144 of the X-ray CT apparatus 10 illustrated in FIG. 8 may or may not have such functions as the acquisition function 144*c*, the model generation function 144*d*, the noise reduction processing function 144*e*, and the output function 144*f*. Furthermore, although FIG. 8 illustrates the X-ray CT apparatus 10 as an example of a medical image diagnostic apparatus, the information processing system 1 may include a medical image diagnostic apparatus different from the X-ray CT apparatus 10. Furthermore, the information processing system 1 may include a plurality of medical image diagnostic apparatuses.

The information processing apparatus 20 performs various processes based on data acquired by the X-ray CT apparatus 10. For example, as illustrated in FIG. 8, the information processing apparatus 20 includes a memory 21, a display 22, an input interface 23, and processing circuitry 24.

The memory 21 can be configured similarly to the aforementioned memory 141. For example, the memory 21 stores a computer program required when circuitry included in the information processing apparatus 20 performs its functions. Furthermore, the memory 21 stores the noise data similarly to the noise pool 141*a*. Furthermore, the memory 21 stores the first subject projection data similarly to the image pool 141*b*. Furthermore, the memory 21 stores the second subject projection data similarly to the image pool 141*c*.

The display 22 can be configured similarly to the aforementioned display 142. For example, the display 22 displays a GUI for receiving various instructions, settings, and the like from a user. Furthermore, for example, the display 22 displays an image based on denoised data in which noise have been reduced by the noise reduction processing model. The information processing apparatus 20 may include a projector instead of or in addition to the display 22.

The input interface 23 can be configured similarly to the aforementioned input interface 143. For example, the input interface 23 receives various input operations from a user, converts the received input operations into electrical signals, and outputs the electrical signals to the processing circuitry 24.

The processing circuitry 24 controls the overall operation of the information processing apparatus 20 by performing a control function 24*a*, an acquisition function 24*b*, a model generation function 24*c*, a noise reduction processing function 24*d*, and an output function 24*e*. For example, the control function 24*a* controls various functions such as the acquisition function 24*b*, the model generation function 24*c*, the noise reduction processing function 24*d*, and the output function 24*e* based on the various input operations received from the user via the input interface 23. The acquisition function 24*b* is a function corresponding to the acquisition function 144*c*. The model generation function 24*c* is a function corresponding to the model generation function 144*d*. The noise reduction processing function 24*d* is a function corresponding to the noise reduction processing function 144*e*. The output function 24*e* is a function corresponding to the output function 144*f*.

In the information processing apparatus 20 illustrated in FIG. 8, respective processing functions are stored in the memory 21 in the form of computer programs that can be executed by a computer. The processing circuitry 24 is a processor that reads and executes the computer programs from the memory 21, thereby performing functions corresponding to the computer programs. In other words, the processing circuitry 24 having read the computer programs has the functions corresponding to the read computer programs.

Note that, in FIG. 8, it has been described that the control function 24*a*, the acquisition function 24*b*, the model generation function 24*c*, the noise reduction processing function 24*d*, and the output function 24*e* are performed by the single processing circuitry 24, but the processing circuitry 24 may be configured by combining a plurality of independent processors, and each processor may be configured to perform each function by executing each computer program.

Furthermore, each processing function of the processing circuitry 24 may be performed by being appropriately distributed or integrated into a single processing circuit or a plurality of processing circuits.

Furthermore, the processing circuitry 24 may also perform the functions by using a processor of an external device connected via the network NW. For example, the processing circuitry 24 reads and executes the computer programs corresponding to the functions from the memory 21 and uses, as computation resources, a server group (cloud) connected to the information processing apparatus 20 via the network NW, thereby performing the functions illustrated in FIG. 8.

For example, based on data acquired from a subject for noise generation obtained by imaging performed by a medical image diagnostic apparatus such as the X-ray CT apparatus 10, the acquisition function 24*b* acquires noise data in the data acquired from a subject for noise generation. Furthermore, based on first subject projection data obtained by the imaging performed by the medical image diagnostic apparatus and the noise data in the data acquired from a subject for noise generation, the acquisition function 24*b* acquires synthesized subject data in which noise based on the noise data are added to the first subject projection data. Furthermore, the model generation function 24*c* obtains a noise reduction processing model by machine learning using the synthesized subject data and second subject projection data obtained by the imaging performed by the medical image diagnostic apparatus. Furthermore, the noise reduction processing function 24*d* reduces noise on input subject data obtained by the imaging performed by the medical image diagnostic apparatus such as the X-ray CT apparatus 10, by the noise reduction processing model, thereby obtaining denoised data. Furthermore, the output function 24*e* outputs an image based on the denoised data.

In another embodiment, when the noise pool 141*a* illustrated in FIG. 4A is generated, noise blocks generated from a noise model can also be included in addition to the above-described noise blocks. For the noise model, a Poisson noise model and/or a Gaussian noise model can be used to simulate image noise. Noise data can be obtained by combining at least two of: the noise data generated from patient CT image data using the method illustrated in FIG. 3A, the noise data generated from water phantom image data using the method illustrated in FIG. 3B, and the noise data generated from at least one of the above-mentioned noise models. For the noise blocks generated from one of the noise models, a scaling factor also can be used to generate various noise data to increase the variety in noise level and noise characteristics in the input images in the training data for training the DCNN described above.

In the method according to the aforementioned embodiment, as training data to be used when training one DCNN, only an image acquired by imaging a specific site (chest, abdomen, head, and the like) may be targeted, instead of targeting all images. In such a case, the DCNN is provided for each site. Alternatively, only an image acquired using imaging parameters/reconstructed parameters (scan protocols) for a specific diagnostic purpose may be targeted. In such a case, the DCNN is prepared for each site or for each diagnostic purpose, for example, for each scan protocol and stored in the memory, and the medical image diagnostic apparatus selects a trained DCNN according to the site selected at the time of imaging and the diagnostic purpose (scan protocol), and performs the noise reduction process on an image, which is acquired by the scan protocol, with the selected DCNN. By so doing, it is possible to achieve effective noise reduction with a DCNN specialized for noise more specific to a specific site or diagnostic purpose (scan protocol).

The term "processor" used in the above description, for example, means a circuit such as a CPU, a graphics processing unit (GPU), an application specific integrated circuit (ASIC), and a programmable logic device (for example, a simple programmable logic device (SPLD), a complex programmable logic device (CPLD), and a field programmable gate array (FPGA)). When the processor is, for example, the CPU, the processor performs functions by reading and executing computer programs stored in a storage circuit. On the other hand, when the processor is, for example, the ASIC, the functions are directly incorporated in the circuit of the processor as a logic circuit instead of storing the computer programs in the storage circuit. Note that each processor of the embodiment is not limited to a case where each processor is configured as a single circuit, and one processor may be configured by combining a plurality of independent circuits to perform functions thereof. Moreover, a plurality of components in each drawing may be integrated into one processor to perform functions thereof.

Furthermore, in FIG. 1A, it has been described that the single memory 141 stores the computer programs corresponding to the respective processing functions of the processing circuitry 144. Furthermore, in FIG. 8, it has been described that the single memory 21 stores the computer programs corresponding to the respective processing functions of the processing circuitry 24. However, the embodiment is not limited thereto. For example, a plurality of memories 141 may be arranged in a distributed manner, and the processing circuitry 144 may be configured to read corresponding computer programs from the individual memories 141. Similarly, a plurality of memories 21 may be arranged in a distributed manner, and the processing circuitry 24 may be configured to read corresponding computer programs from the individual memories 21. Furthermore, instead of storing the computer programs in the memory 141 or the memory 21, the computer programs may be directly incorporated in the circuit of the processor. In such a case, the processor reads and executes the computer programs incorporated in the circuit to perform functions thereof.

Each component of each apparatus according to the aforementioned embodiment is functionally conceptual, and does not necessarily need to be physically configured as illustrated in the drawings. That is, the specific form of distribution and integration of each apparatus is not limited to that illustrated in the drawing and all or some thereof can be functionally or physically distributed and integrated in arbitrary units according to various loads, usage conditions, and the like. Moreover, all or some of the processing functions performed by each apparatus may be performed by the CPU and the computer programs that are analyzed and executed by the CPU, or may be performed as a wired logic-based hardware.

Furthermore, the information processing method described in the aforementioned embodiment can be implemented by executing an information processing program prepared in advance on a computer such as a personal computer and a workstation. The information processing program can be distributed via a network such as the Internet. Furthermore, the information processing program can be executed by being recorded on a non-transitory computer readable recording medium such as a hard disk, a flexible disk (FD), a CD-ROM, an MO, and a DVD, and being read from the recording medium by the computer.

According to at least one embodiment described above, it is possible to easily acquire a high-quality noise reduction processing model.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An information processing method for information acquired by imaging performed by a medical image diagnostic apparatus, the information processing method comprising:

acquiring a training image volume including at least one three-dimensional object having an embedded three-dimensional feature having a first cross-sectional area in a first three-dimensional plane;

determining, by rotating the first three-dimensional plane, a second three-dimensional plane different from the first three-dimensional plane, and containing the embedded three-dimensional feature so that a second cross-sectional area of the embedded three-dimensional feature in the second three-dimensional plane is larger than the first cross-sectional area;

generating, from the acquired training image volume, a first image along the first three-dimensional plane and a second image along the second three-dimensional plane; and training an untrained neural network for each part of a plurality of body parts with the first and second images generated from the acquired training image volume.

2. The method according to claim 1, wherein the first three-dimensional plane is orthogonal to the second three-dimensional plane.

3. The method according to claim 1, wherein the second three-dimensional plane is determined to provide a maximum cross-sectional area of the embedded three-dimensional feature.

4. The method according to claim 1, wherein the embedded three-dimensional feature is a stent.

5. The method according to claim 1, wherein the training image volume comprises image data reconstructed from CT projection data.

6. An apparatus for an information processing method for information acquired by imaging performed by a medical image diagnostic apparatus, comprising:

processing circuitry configured to:

acquire a training image volume including at least one three-dimensional object having an embedded three-dimensional feature having a first cross-sectional area in a first three-dimensional plane;

determine, by rotating the first three-dimensional plane, a second three-dimensional plane different from the first three-dimensional plane, and containing the embedded three-dimensional feature so that a second cross-sectional area of the embedded three-dimensional feature in the second three-dimensional plane is larger than the first cross-sectional area;

generate, from the acquired training image volume, a first image along the first three-dimensional plane and a second image along the second three-dimensional plane; and train an untrained neural network for each part of a plurality of body parts with the first and second images generated from the acquired training image volume.

7. The apparatus according to claim 6, wherein the first three-dimensional plane is orthogonal to the second three-dimensional plane.

8. The apparatus according to claim 6, wherein the second three-dimensional plane is determined to provide a maximum cross-sectional area of the embedded three-dimensional feature.

9. The apparatus according to claim 6, wherein the embedded three-dimensional feature is a stent.

10. The apparatus according to claim 6, wherein the training image volume comprises image data reconstructed from CT projection data.

* * * * *